United States Patent
Dahne et al.

(10) Patent No.: US 11,497,940 B2
(45) Date of Patent: Nov. 15, 2022

(54) HAIR TREATMENT METHOD AND KIT THEREOF

(71) Applicant: Noxell Corporation, Hunt Valley, MD (US)

(72) Inventors: Lars Siegfried Dahne, Berlin (DE); Mathias Kurt Herrlein, Kronberg (DE); Stephen Robert Schofield, Egham (GB); Cagri Uzum, Berlin (DE); Natascha Katharina Schelero, Hattersheim (DE)

(73) Assignee: WELLA OPERATIONS US, LLC, Calabasas, CA (US)

( * ) Notice: Subject to any disclaimer, the term of this patent is extended or adjusted under 35 U.S.C. 154(b) by 0 days.

(21) Appl. No.: 16/095,845

(22) PCT Filed: Apr. 25, 2017

(86) PCT No.: PCT/US2017/029427
§ 371 (c)(1),
(2) Date: Oct. 23, 2018

(87) PCT Pub. No.: WO2017/189585
PCT Pub. Date: Nov. 2, 2017

(65) Prior Publication Data
US 2019/0201720 A1 Jul. 4, 2019

(30) Foreign Application Priority Data
Apr. 25, 2016 (EP) ..................... 16166945

(51) Int. Cl.
*A61Q 5/08* (2006.01)
*A61K 8/41* (2006.01)
*A61K 8/73* (2006.01)
*A61K 8/81* (2006.01)
*A61K 8/84* (2006.01)

(52) U.S. Cl.
CPC .............. *A61Q 5/08* (2013.01); *A61K 8/416* (2013.01); *A61K 8/731* (2013.01); *A61K 8/817* (2013.01); *A61K 8/8117* (2013.01); *A61K 8/84* (2013.01); *A61K 2800/5424* (2013.01); *A61K 2800/5426* (2013.01); *A61K 2800/594* (2013.01); *A61K 2800/88* (2013.01); *A61K 2800/884* (2013.01)

(58) Field of Classification Search
CPC .... A61K 2800/5424; A61K 2800/5426; A61K 2800/594; A61K 2800/88; A61K 2800/884; A61K 8/416; A61K 8/731; A61K 8/8117; A61K 8/817; A61K 8/84; A61Q 5/08
See application file for complete search history.

(56) References Cited

U.S. PATENT DOCUMENTS 4,638,822 A * 1/1987 Grollier ................. A61K 8/731
132/209

FOREIGN PATENT DOCUMENTS

| BR | WO 2001/064180 A1 * | 9/2001 | ............ A61K 7/50 |
|---|---|---|---|
| CA | 2841730 A1 | 8/2014 | |
| GB | 2123694 A | 2/1984 | |
| GB | 2383950 A | 7/2003 | |
| JP | 2007001880 A | 1/2007 | |
| WO | WO-2015122029 A1 | 8/2015 | |

OTHER PUBLICATIONS

"European Application Serial No. 16166945.2, Communication Pursuant to Article 94(3) EPC dated Nov. 7, 2018", 3 pgs.
"International Application Serial No. PCT US2017 029427, International Preliminary Report on Patentability dated Nov. 8, 2018", 9 pgs.
"European Application Serial No. 16166945.2, Extended European Search Report dated Aug. 31, 2016", 8 pgs.
"European Application Serial No. 16166945.2, Response filed May 9, 2019 to Communication Pursuant to Article 94(3) EPC dated Nov. 7, 2018", w/ English Claims, 18 pgs.

* cited by examiner

*Primary Examiner* — Jeffrey T. Palenik
(74) *Attorney, Agent, or Firm* — Dennemeyer & Associates; Victoria Friedman

(57) ABSTRACT

Method for treating hair comprising the successive application onto hair of polymeric layers which can be removed to a large extent or even totally in an easy manner upon request of the user by using a cationic surfactant.

17 Claims, No Drawings

HAIR TREATMENT METHOD AND KIT THEREOF

CROSS-REFERENCE TO RELATED APPLICATION

This application is a U.S. National Stage Filing under 35 U.S.C. 371 from International Application No. PCT/US2017/029427, filed on Apr. 25, 2017, and published as WO 2017/189585 on Nov. 02, 2017, which claims the benefit of priority to European Application No. 16166945.2, filed on Apr. 25, 2016, which applications are incorporated by reference herein in their entirety.

FIELD OF THE INVENTION

The invention is directed to a method for treating hair comprising the successive application onto hair of polymeric layers which can be removed to a large extent or even totally in an easy manner upon request of the user.

BACKGROUND OF THE INVENTION

Different methods for changing the natural colour of hair are known in the art These methods involve the use of hair colouring compositions which allow either permanent or temporary change of hair colour. Hair colouring compositions which are used to permanently change the colour of hair, also called oxidative hair colouring compositions, typically comprise oxidative hair dye precursors, which can diffuse into the hair through the cuticle and into the cortex where they then react with each other and a suitable oxidizing agent to form the end dye molecules. Due to their larger size, the resultant molecules are unable to readily diffuse out of the hair during subsequent washing with water and/or detergents; hence delivering a consumer-desired permanency of colour. This reaction typically takes place at approximately pH 10 to 11 in the presence of an alkalizing agent and an oxidizing agent. Typically an oxidizing composition (also called developer and/or oxidizing component) comprising the oxidizing agent and a dye composition (also called tint or dye component) comprising the alkalizing agent and if present the hair dye precursors are mixed shortly before use. The consumer repeats this process regularly in order to maintain the desired hair colour, shade and intensity of colour and to ensure continual, even coverage of the hair including coverage of new hair growth. The problem with standard oxidative hair colouring methods is that the conditions under which the reaction is taking place, i.e. the high pH value as well as the presence of an oxidizing agent may cause damage to the structure of the hair and may he irritating for the scalp of the user, especially when such a process is repeated regularly and the compositions which are usually used have an undesirable odour. Furthermore, obtaining the desired colour result is not easy since standard oxidative hair colouring compositions are reactive compositions and it is therefore not easy to control the reaction on hair. Finally, once the hair has been coloured with oxidative hair colouring compositions, it is particularly difficult for the user to remove totally the colour or even to a large extent, e.g. to retrieve its natural hair colour. In order to do so, the user would typically need to either colour its hair with a new oxidative hair colouring composition or wait for the new hair to grow.

Alternatively, methods for temporarily changing the colour of hair have also been developed. These methods usually involve the application of hair colouring compositions comprising direct dyes. Direct dye compositions are usually less aggressive for the hair since they are non reactive compositions. However, since direct dyes are low molecular weight molecules, they may have the tendency to also colour the scalp of the user. Even if the hair colouration which is obtained is typically characterized by a weaker washfastness than when the hair is coloured with standard oxidative hair colouring compositions, i.e. the colouration is typically fading after regular washing of the hair with standard shampoo compositions, it may still be difficult or at least requires a lot of time for the user to remove the colour at least to a large extent, if not entirely.

Methods for temporarily changing the colour of hair involving the application of hair colouring compositions comprising polymeric dyes have also been developed. The hair colouration which is obtained by application of polymeric dyes onto hair is also typically characterized by a weaker washfastness than when the hair is coloured with standard oxidative hair colouring compositions. However, it may also be difficult or at least require a lot of time for the user to remove the colour at least to a large extent, if not entirely.

Therefore, there is still the need for a method for treating hair which makes easier the removal upon request of the user of an artificial colouration which is obtained thereafter on hair. This method should preferably involve the use of compositions which are less aggressive for the hair and for the scalp. Finally, this method should also preferably involve the use of low odour compositions.

The inventors have surprisingly found that at least some of these needs may be met by the method for treating hair according to the present invention, wherein a polymeric layer is obtained onto the hair by successively applying a cationic polymer and an anionic polymer prior to colouring the hair and wherein a portion of this polymeric layer and therefore any artificial colouration that is obtained thereafter on hair can be removed upon request of the user by using a cationic surfactant.

SUMMARY OF THE INVENTION

The present invention relates to a method for treating hair comprising:
A) carrying out the following sequence of steps:
  i) applying a first composition comprising one or more first cationic polymer(s) to a first portion of the hair; and
  ii) applying a second composition comprising one or more first anionic polymer(s) to a second portion of the hair; and
B) applying a third composition comprising one or more cationic surfactant(s) to a third portion of hair, preferably wherein the cationic surfactant(s) comprise one or more linear or branched group(s) comprising at least 8 carbon atoms, more preferably one or more linear or branched group(s) comprising from 8 to 22 carbon atoms, even more preferably one or more linear or branched group(s) comprising from 10 to 22 carbon atoms, most preferably one or more linear or branched group(s) comprising from 16 to 22 carbon atoms,
wherein the first, second and third portions have at least one first common area.

The present invention also relates to a kit for treating hair comprising a first component comprising the first composition as defined hereinbefore, a second component comprising the second composition as defined hereinbefore and a third component comprising the third composition as defined hereinbefore.

DETAILED DESCRIPTION OF THE INVENTION

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

All ratios or percentages are weight ratios or weight percentages unless specifically stated otherwise.

By "cationic polymer" it is meant any polymer comprising an overall charge at full protonation which is positive.

By "cationic coloured polymer" it is meant any cationic polymer comprising at least one chromophore and/or at least one fluorophore either in the skeleton or as pendent group.

By "cationic uncoloured polymer" it is meant any cationic polymer which does not comprise any chromophore or fluorophore either in the skeleton or as pendent group.

By "anionic polymer" it is meant any polymer comprising an overall charge at full deprotonation which is negative.

By "anionic coloured polymer" it is meant any anionic polymer comprising at least one chromophore and/or at least one fluorophore either in the skeleton or as pendent group.

By "anionic uncoloured polymer" it is meant any anionic polymer which does not comprise any chromophore or fluorophore either in the skeleton or as pendent group.

By "full protonation" it is meant the state at which the different protonable groups of a polymer are all fully protonated.

By "full deprotonation" it is meant the state at which the different deprotonable groups of a polymer are all fully deprotonated.

By "weak cationic polymer" it is meant a cationic polymer whose charge is dependent on the pH when solubilized in water.

Method for Treating Hair

The present invention relates to a method for treating hair as stated hereinbefore, Having art least one common area between the first portion of the hair to which the first composition is applied and the second portion of the hair to which the second composition is applied ensures that at least a portion of the second composition is applied to the same portion of the hair as at least a portion of the first composition. In this portion of the hair a polymeric layer made of an anionic polymeric sublayer positioned on top of a cationic polymeric sublayer is obtained after the successive application of the first cationic polymer(s) and the first anionic polymer(s). This polymeric layer is hereinafter referred to as the first polymeric layer.

Hair is naturally negatively charged. Therefore, the inner sublayer of the coated hair which is positively charged can easily attach to the surface of the hair and the outer sublayer of the coated hair which is negatively charged can easily attach to the surface of the cationic polymeric sublayer positioned underneath. Since the outer sublayer of the coated hair has an electrostatic structure similar to the one of the outer layer of natural hair, it is possible to apply any further hair treatment on top of the first polymeric layer that would usually be directly applied onto hair.

While not wishing to be bound by theory, it is believed that having at least one common area between the first portion of the hair to which the first composition is applied and the second portion of the hair to which the second composition is applied and the third portion of the hair to which the third composition is applied, ensures that the third composition comprising the cationic surfactant(s) enters into contact with the first polymeric layer and therefore helps to remove at least a part of the first polymeric layer and therefore any layer, e.g. a coloured layer which can be obtained on top of the first polymeric layer during a subsequent step.

Therefore, the method according to the present invention is particularly advantageous since it is a simple way for treating the hair to make easier the removal of any artificial colouration that is obtained thereafter on hair. Furthermore, the compositions which are used in the method according to the present invention are particularly advantageous since these compositions exhibit low odour.

First Composition

The first composition may be applied all over the hair.

The first composition may be applied in one go or step-by-step to the hair. The first composition may be applied step-by-step, for example in case the hair is damaged. Applying the first composition step-by-step, may help to ensure that the hair is saturated with the first composition and may therefore provide a better coverage of the hair with the first composition.

First Cationic Polymer(s)

The first composition comprises one or more first cationic polymer(s).

The first cationic polymer(s) may be coloured.

The first cationic polymer(s) may preferably be uncoloured.

The first cationic polymer(s) may comprise one or more amino functional group(s) per polymer chain, wherein the amino functional group(s) are selected from the group consisting of primary, secondary, tertiary, quaternary amino functional groups and mixtures thereof, preferably from the group consisting of secondary, tertiary, quaternary amino functional groups and mixtures thereof, more preferably from quaternary amino functional groups.

The first cationic polymer(s) may be selected from the group consisting of polyethyleneimine, polyallylamine hydrochloride, polydiallyldimethylammonium chloride, polyvinylamine, copolymers thereof and mixtures thereof. The first cationic polymer(s) may preferably be selected from the group consisting of polyethyleneimine, polydiallyldimethylammonium chloride, copolymers thereof and mixtures thereof.

The copolymers may be random or block copolymers.

The first cationic polymer(s) may be linear or branched.

The first cationic polymer(s) may be selected from the group consisting of:

a) Linear polyethyleneimine of the formula:

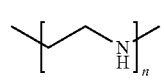

in which n is an integer representing the degree of polymerization, wherein n ranges from 50 to 20,000, alternatively from 100 to 3,500;

b) Branched polyexyleneimine consisting of primary, secondary and tertiary amine groups of the formula:

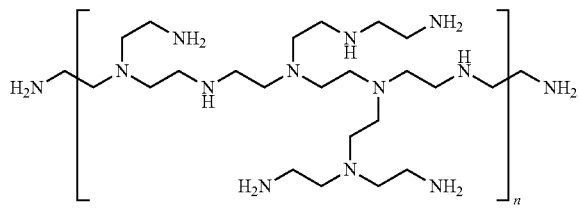

in which n is an integer representing the degree of polymerization, wherein n ranges from 5 to 4,000, alternatively from 50 to 500;

c) Polyallylamine hydrochloride of the formula:

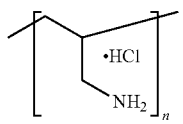

in which n is an integer representing the degree of polymerization, wherein n ranges from 50 to 20,000, alternatively from 150 to 2000;

d) Polydiallyldimethylammonium chloride of the formula:

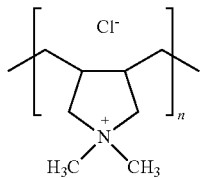

in which n is an integer representing the degree of polymerization, wherein n ranges from 10 to 20,000, alternatively from 150 to 4,000; copolymers thereof and mixtures thereof.

The copolymers may be random or block copolymers.

The first cationic polymer(s) may have a charge density at full protonation of at least 0.3, preferably at least 0.6, more preferably at least 0.8, even more preferably at least 1.0 positive charges per monomer unit.

The first cationic polymer(s) may have a weight average molecular weight of more than 0.5 kD, preferably from 0.5 kD to 5000 kD, more preferably from 2 kD to 1000 kD, even more preferably from 10 kD to 200 kD, most preferably from 25 kD to 70 kD.

Second Composition

The second composition may be applied all over the hair.

The second composition is applied after the first composition to the hair.

The second composition may be applied in one go or step-by-step to the hair. The second composition may be applied step-by-step, for example in case the hair is damaged. Applying the second composition step-by-step, may help to ensure that the hair is saturated with the second composition and may therefore provide a better coverage of the hair with the second composition.

First Anionic Polymer(s)

The second composition comprises one or more first anionic polymer(s).

The first anionic polymer(s) may be coloured.

The first anionic polymer(s) may preferably be uncoloured.

The first anionic polymer(s) may comprise one or more functional group(s) per polymer chain selected from the group consisting of phenyl group, alkyl groups comprising at least 8 carbon atoms and mixtures thereof.

The first anionic polymer(s) may be selected from the group consisting of polystyrene sulfonate salts, λ-carrageenan salts, dextran sulfate salts, polyacrylic acid salts, poly(methacrylic acid) salts, alginic acid salts, carboxymethylcellulose salts, polystyrene sulfonate/polystyrene copolymer salts, copolymers thereof and mixtures thereof. The first anionic polymer(s) may preferably be selected from the group consisting of polystyrene sulfonate salts, polystyrene sulfonate/polystyrene copolymer salts, copolymers thereof and mixtures thereof.

The copolymers may be random or block copolymers.

The first anionic polymer(s) may be linear or branched.

The anionic polymers may be selected from the group consisting of:

a) Polystyrene sulfonate (PSS) sodium salt of the formula:

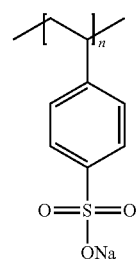

in which n is an integer representing the degree of polymerization, wherein n ranges from 50 to 20,000, alternatively from 150 to 2500;

b) Co-polymer of polystyrene sulfonate (PSS) sodium salt and poly(4-styrenesulfonic acid-co-maleic acid) of the formula:

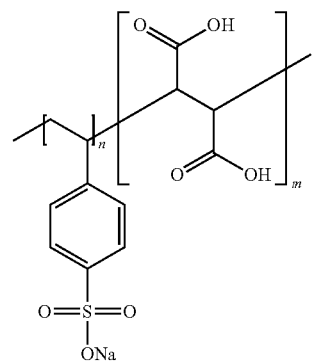

in which n and m are integers representing the degree of polymerization, wherein n+m ranges from 50 to 20,000, alternatively from 150 to 2500;
c) λ-Carrageenan;
d) Dextran sulfate sodium salt;
e) Polyacrylic acid (PAA) of the formula:

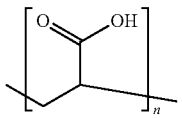

in which n is an integer representing the degree of polymerization, wherein n ranges from 50 to 20,000, alternatively from 150 to 1,000;
f) Alginic acid sodium salt;
g) Carboxymethylcellulose sodium salt of the formula:

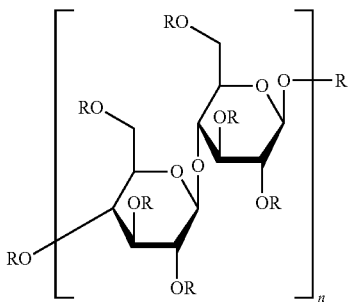

in which:
R is H or $(CH_2)_2COONa$ and
n is an integer representing the degree of polymerization;
copolymers thereof and mixtures thereof.

The copolymers may be random or block copolymers.

The first anionic polymer(s) may have a charge density at full deprotonation of at least 0.3, alternatively at least 0.6, alternatively at least 0.8, alternatively at least 1.0 negative charges per monomer unit.

The first anionic polymer(s) may have a weight average molecular weight of at least 1 kD, alternatively from 10 kD to 1000 kD, alternatively from 70 to 500 kD.

First and Second Compositions

The first cationic polymer(s) and the first anionic polymer(s) may preferably be uncoloured. The first and the second portions of the hair may be the same. The first and the second compositions may be applied all over the hair.

Third Composition

The third composition may be applied all over the hair. Step B) is carried out after step A). Step B) may be carried out immediately after step A) or at least 1 hour after step A) or at least 24 hours after step A) or at least 10 days after step A) or at least one month after step A).

Cationic Surfactant(s)

The third composition comprises one or more cationic surfactant(s). The cationic surfactant(s) may preferably comprise one or more linear or branched group(s) comprising at least 8 carbon atoms. The cationic surfactant(s) may more preferably comprise one or more linear or branched group(s) comprising from 8 to 22 carbon atoms. The cationic surfactant(s) may even more preferably comprise one or more linear or branched group(s) comprising from 10 to 22 carbon atoms. The cationic surfactant(s) may most prefer- ably comprise one or more linear or branched group(s) comprising from 16 to 22 carbon atoms. The linear or branched group(s) may optionally comprise at least one heteroatom selected from oxygen, nitrogen, sulfur and halogens. The linear or branched groups may be aliphatic groups.

While not wishing to be bound by theory, it is believed that the interaction between the cationic surfactant(s) comprised in the third composition and the first anionic polymer(s) may be stronger than the interaction between the first anionic polymer(s) and the first cationic polymer(s) inside the first polymeric layer and therefore may help to remove a part of the first polymeric layer, i.e. a part of the anionic polymeric sublayer.

While not wishing to be bound by theory, it is believed that the interaction between the cationic surfactant(s) comprised in the third composition and the first anionic polymer(s) may be even stronger when the first anionic polymer(s) are more hydrophobic, e.g. when the first anionic polymer(s) comprise one or more functional group(s) per polymer chain selected from the group consisting of phenyl group, alkyl groups comprising at least 8 carbon atoms and mixtures thereof.

The cationic surfactant(s) may be selected from the group consisting of quaternary ammonium salts, amido-amines, primary amines, secondary amines, tertiary amines and mixtures thereof.

The cationic surfactants) may be selected from quaternary ammonium salts having the following formula:

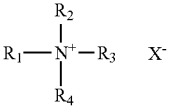

wherein:
$R_1$ is selected from the group consisting of linear or branched groups optionally comprising at least one heteroatom selected from oxygen, nitrogen, sulfur and halogens, wherein the linear or branched groups comprise from 6 to 22 carbon atoms, preferably from 16 to 22 carbon atoms; and $R_2$ is selected from the group consisting of linear or branched groups optionally comprising at least one heteroatom selected from oxygen, nitrogen, sulfur and halogens, wherein the linear or branched groups comprise from 1 to 22 carbon atoms, preferably from 16 to 22 carbon atoms, aryl groups and alkylaryl groups; and $R_3$ and $R_4$ are independently selected from the group consisting of linear or branched groups comprising from 1 to 4 carbon atoms, aryl groups and alkylaryl groups; and $X^-$ is an anion selected from chloride, bromide, iodide, alkyl sulfates, phosphates, alkyl sulfonates, alkylaryl sulfonates and anions derived from organic acids or amino acids.

The linear or branched groups may be aliphatic groups. The aliphatic groups may be selected from alkyl, alkoxy and alkylamide groups.

The amino acid may be glutamic acid. The anions derived from organic acids may be acetate anions or lactates anions.

The cationic surfactant(s) may be selected from aminoamines having the following formula:

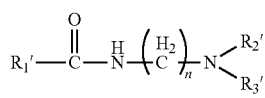

wherein:
- $R_1'$ is selected from the group consisting of linear or branched groups optionally comprising at least one heteroatom selected from oxygen, nitrogen, sulfur and halogens, wherein the linear or branched groups comprise from 10 to 22 carbon atoms, preferably from 16 to 22 carbon atoms;
- $R'_2$ and $R'_3$ are independently selected from the group consisting of hydrogen, linear or branched groups optionally comprising at least one heteroatom selected from oxygen, nitrogen, sulfur and halogens, wherein the linear or branched groups comprise from 1 to 4 carbon atoms, acyl groups and alkylaryl groups;
- n is integer ranging from 1 to 4.

The linear or branched groups may be aliphatic groups. The aliphatic groups may be selected from alkyl, alkoxy and alkylamide groups.

The cationic surfactant(s) may be selected from the group consisting of cetrimonium halide, stearimonium halide, behentrimonium halide, behentrimonium halide, stearamidopropyltrimonium halide, dodecyltrimethylammonium halide, didodecyldimethylammonium halide, tetradecyltrimethyammonium halide, distearyldimethylammonium halide, dicetyldimethylammonium halide, distearoylethyl dimonium halide, behenamidopropyltrimonium methosulfate, behenamidopropyl dimethylamine, stearamidopropyl dimethylamine, behenamidopropyl diethylamine, behenamidoethyl diethylamine, behenamidoethyl dimethylamine, arachidamidopropyl dimethylamine, arachidamidopropyl diethylamine, arachidamidoethyl diethylamine, arachidamidoethyl dimethylamine, and mixtures thereof, wherein the halide is selected from bromide and chloride. The cationic surfactant(s) may preferably be selected from the group consisting of dodecyltrimethylammonium halide, didodecyldimethylammonium halide, tetradecyltrimethylammonium halide, cetrimonium halide and mixtures thereof, wherein the halide is selected from bromide and chloride.

The third composition comprises a total amount of cationic surfactants ranging from 0.01% to 10%, preferably from 0.05% to 5%, more preferably from 0.3% to 3% by total weight of the third composition. The amount of each particular cationic surfactant or mixtures thereof described hereinbefore can account for up to 100% (or 100%) of the total amount of cationic surfactants in the third composition.

The third composition comprises one or more cationic surfactant(s) and may have a pH of at least 8.5 and/or may comprise one or more oxidizing agent(s).

pH

The third composition may have a pH of at least 8.5, The third composition may have a pH ranging from 8.5 to 14, preferably from 9 to 14, more preferably from 10 to 12, even more preferably from 10.5 to 11.5. In such embodiments, the first cationic polymer(s) may preferably be weak cationic polymers.

The third composition may be selected from the group consisting of an aqueous solution, an oil-in-water emulsion and a water-in-oil emulsion. The third composition may preferably be an aqueous solution. In the embodiments wherein the third composition is an oil-in-water emulsion or a water-in-oil emulsion, the pH of the third composition corresponds to the pH of the aqueous phase.

While not wishing to be bound by theory, it is believed that the high pH of the third composition may help to lower the overall charge of the first cationic polymer(s) when the first cationic polymer(s) are weak cationic polymers and weaken the interaction between the first anionic polymer(s) and the first cationic polymer(s) inside the first polymeric layer and therefore may help to remove a part of the first polymeric layer, i.e. a part of the anionic polymeric sublayer. While not wishing to be bound by theory, it is also believed that the high pH of the third composition may help to lower the overall charge of the first cationic polymer(s) and also weaken the interaction between the first cationic polymer(s) and the surface of the hair.

pH Modifier and/or Buffering Agent

The third composition may comprise at least one pH modifier and/or buffering agent selected from the group consisting of ammonia, alkanolamines, guanidium salts, alkali metal hydroxides, alkali metal carbonates, ammonium hydroxides, ammonium carbonates, inorganic acids, organic acids and mixtures thereof. The pH modifier and/or buffering agent may preferably be selected from the group consisting of alkanolamines, guanidium salts, alkali metal hydroxides, alkali metal carbonates, inorganic acids, organic acids and mixtures thereof.

The alkanolamines may be selected from the group consisting of monoethanolamine, diethanolamine, triethanolamine, monopropanolamine, dipropanolamine, tripropanolamine, 2-amino-2-methyl-1-propanol, 2-amino-2-hydroxymethyl-1,3,-propandiol and mixtures thereof.

The inorganic or organic acids may be selected from the group consisting of phosphoric acid, acetic acid, ascorbic acid, citric acid or tartaric acid, hydrochloric acid and mixtures thereof.

Oxidizing Agent(s)

The third composition may comprise one or more oxidizing agent(s). The oxidizing agent(s) may preferably be selected from the group consisting of hypochlorous acid, peracetic acid, persulfate, chlorine dioxide, perboric acid, salts thereof, ozone, hydrogen peroxide and mixtures thereof. The oxidizing agent(s) may more preferably be selected from the group consisting of hypochlorous acid, salts thereof and mixtures thereof. The oxidizing agent(s) may even more preferably be selected from the group consisting of sodium hypochlorite, calcium hypochlorite, potassium hypochlorite and mixtures thereof.

While not wishing to be bound by theory, it is believed that the oxidizing agent(s) comprised in the third composition may help to remove a part of the first polymeric layer.

The third composition may comprise a total amount of oxidizing agents selected from the group consisting of sodium hypochlorite, calcium hypochlorite, potassium hypochlorite and mixtures thereof of up to 25% by total weight of the third composition. The third composition may comprise a total amount of oxidizing agents selected from the group consisting of sodium hypochlorite, calcium hypochlorite, potassium hypochlorite and mixtures thereof ranging from 0.01% to 10%, preferably from 0.2% to 2%, more preferably from 0.5% to 1.5% by total weight of the third composition. The amount of each particular oxidizing agent or mixtures thereof described hereinbefore can account for up to 100% (or 100%) of the total amount of oxidizing agents in the third composition.

The third composition may be a shampoo composition, a hair conditioning composition or a hair treatment composition.

First, Second and Third Compositions

The first, the second and the third portions of the hair may be the same. The first, the second and the third compositions may be applied all over the hair.

Additional Steps

Removal of the Excess of the Compositions

At least one of steps i), ii) or B), preferably all the steps i), ii) and B) may further comprise the subsequent sub-step of removing the excess of the respective composition(s) with fingers and/or a towel.

Application of Energy

Steps i) and/or ii) may further comprise the subsequent sub-step of applying energy to the hair in the form of heat, ultrasounds, infrared and/or microwaves. This sub-step may be carried out either after the application of the first or second composition to the hair or after removing the excess of the first composition or the second composition from the hair. While not wishing to be bound by theory, it is believed that applying energy to the hair may accelerate the speed of formation of the polymeric sublayers on the hair and therefore may increase the stability of the sublayers once they are formed on the hair. The hair may be heated to a temperature ranging from 5° C. to 70° C., alternatively 20° C. to 60° C., alternatively 40° C. to 60° C.

Washing and/or Rinsing

At least one of steps i), ii) or B), preferably all the steps i), ii) or B) may further comprise the subsequent sub-step of washing and/or rinsing the hair, preferably with a liquid selected from the group consisting of a cosmetically acceptable solvent, a solution comprising a cosmetically acceptable solvent and a cosmetically acceptable salt, a shampoo composition and mixtures thereof, more preferably with water.

Pre-treatment

The hair may be pretreated prior to step i) to modify the number of positive or negative charges in some portions of the hair or all over the hair. This pretreatment may be done using chemical or physical means such as pH change, oxidation, reduction, bleaching, plasma treatment, ozone treatment, electrowetting, dry or wet ion-treatment.

Hair Colouring Step

The method according to the present invention may further comprise the step of colouring the hair by applying hair colouring composition(s). The hair colouring composition(s) may comprise coloured polymer(s) or pigment(s). The hair colouring composition(s) may form coloured layer(s) after application onto the hair.

The method may further comprise between steps A) and B) step a) of applying a fourth composition comprising one or more second cationic polymer(s) and/or one or more pigment(s), preferably one or more second cationic polymer(s) to a fourth portion of the hair, wherein the fourth portion of the hair has at least one common area with the first common area and the second cationic polymer(s) are cationic coloured polymers.

Having at least one common area between the fourth portion of the hair to which the fourth composition is applied and the first common area defined hereinbelow ensures that the fourth composition is applied to the same portion of the hair wherein the first polymeric layer is obtained after the successive application of the first cationic polymer(s) and the first anionic polymer(s). While not wishing to be bound by theory it is believed that this also ensures that the third composition is also applied to the portion of the hair comprising the first polymeric layer and the coloured layer on top of it and therefore helps to remove at least a part of the first polymeric layer and at least the part of the coloured layer which is obtained on top of the part of the first polymeric layer that is removed. While not wishing to be bound by theory, it is believed that the part of the first polymeric layer that is removed is a part of the anionic polymeric sublayer, the interaction between the cationic surfactant(s) comprised in the third composition and the first anionic polymer(s) being stronger than the interaction between the first anionic polymer(s) and the first cationic polymer(s) inside the first polymeric layer.

The fourth portion of the hair may be the same as the first common area.

The fourth composition may be applied all over the hair.

Step B) may be carried out immediately after step a) or at least 1 hour after step a) or at least 24 hours after step a) or at least 10 days after step a) or at least one month after step a).

Alternatively, the method may further comprise between steps A) and B) the step a) of carrying out the following sequence of steps:

$a_1$) applying a fourth composition comprising one or more second cationic polymer(s) to a fourth portion of the hair; and $a_2$) applying a fifth composition comprising one or more second anionic polymer(s) to a fifth portion of the hair; wherein the fourth and the fifth portions of the hair have at least one second common area.

The fifth composition is applied after the fourth composition to the hair.

Having at least one second common area between the fourth portion of the hair to which the fourth composition is applied and the fifth portion of the hair to which the fifth composition is applied ensures that at least a portion of the fifth composition is applied to the same portion of the hair as at least a portion of the fourth composition.

The fourth and the fifth portions of the hair may be the same.

The fourth and/or the fifth compositions may be applied all over the hair.

The method may further comprise between steps A) and B) the optional step b) of repeating step a) at least once, wherein the second common area of each of the repeated steps a) has at least one third common area with the second common area of step a) and the second common area of each of the other repeated steps a), in case step a) is repeated more than once. This ensures that at least a portion of each of the fourth and fifth compositions which are applied to the hair in each of the sequences of steps is applied to the same portion of the hair.

In step a) and/or in at least one of the repeated steps a), the second cationic polymer(s) are cationic coloured polymers and/or the second anionic polymer(s) are anionic coloured polymers.

The first and the second common areas have at least one common area and/or the first and the third common areas have at least one common area.

Having at least one common area between the first and the second common areas and/or between the first and the third common areas ensures that the fourth and the fifth compositions are successively applied to the same portion of the hair wherein the first polymeric layer is obtained. While not wishing to be bound by theory it is believed that this also ensures that the third composition is also applied to the portion of the hair comprising the first polymeric layer and the coloured layer(s) on top of it and therefore helps to remove at least a part of the first polymeric layer and at least the part of the coloured layer(s) which is obtained on top of the part of the first polymeric layer that is removed. While not wishing to be bound by theory, it is believed that the part of the first polymeric layer that is removed is a part of the anionic polymeric sublayer, the interaction between the cationic surfactant(s) comprised in the third composition and the first anionic polymer(s) being stronger than the interaction between the first anionic polymeric sublayer and the first cationic polymeric sublayer inside the first polymeric layer.

The first and the second common areas may be the same and/or the first and the third common areas may be the same.

Step B) may be carried out immediately after step a) or b) or at least 1 hour after step a) or b) or at least 24 hours after step a) or b) or at least 10 days after step a) or b) or at least one month after step a) or b).

Each of the fourth compositions of step a) and of the repeated steps a) may be the same or different. Each of the fifth compositions of step a) and of the repeated steps a) may be the same or different.

In step a) and/or in each of the repeated step a), the fourth and the fifth compositions may applied all over the hair.

In step b), step a) may be repeated at least at least twice, alternatively at least three times. Alternatively, in step b), step a) may be repeated from 1 to 3 times.

Having a hair colouring step as stated hereinbefore is particularly advantageous. Indeed, by carrying out this hair colouring step, it is possible to provide the hair with the desired colour result and colour intensity in an easy manner. The method is unique in that in each of the sequence of steps a fifth composition comprising one or more second anionic polymer(s) is applied to the hair after a fourth composition comprising one or more second cationic polymer(s) has been applied to the hair.

Since the cationic polymer(s) and the anionic polymer(s) which are comprised in respectively the fourth composition and the fifth composition are high molecular weight molecules, they usually do not diffuse into the hair or at least only to a limited extent when compared with dyes used in standard oxidative hair colouring methods. They usually form polymeric layers on hair which are placed on top of each other by alternating the deposition of the cationic polymer(s) and the anionic polymer(s). By performing the sequence of steps of the hair colouring step more than once it is possible to obtain more than two polymeric layers on hair and therefore to have a better control on the final colour result and colour intensity which is obtained. By increasing the number of layers which are applied to the hair it is possible to obtain hair colorations having increased colour intensity. The user may decide on how many times the sequence of steps should be repeated and therefore have a better control over the colour result which is obtained on hair.

Furthermore, it is particularly advantageous to apply a fifth composition comprising one or more second anionic polymer(s) to the hair after having applied a fourth composition comprising one or more second cationic polymer(s). Indeed, the polymer(s) which are comprised in the fifth composition are negatively charged and therefore the outer layer of the coated hair has an electrostatic structure which is similar to the one of the outer layer of natural hair. Therefore it is possible to apply standard cationic conditioners to the hair after this hair coloring step.

It is particularly important for the hair colouring step to have an anionic polymeric layer which is positioned on top of the cationic polymeric layer. Indeed, the presence of the anionic layer is essential in order to have the possibility of applying a subsequent cationic layer on top of it when the sequence of steps of the hair colouring step is carried out more than once. While not wishing to be bound by theory it is also believed that in some embodiments, the anionic polymeric layer may act as a protective layer for the cationic coloured layer which is placed underneath and therefore may contribute to the good washfastness of the hair coloration.

Furthermore, the compositions which are used in the hair colouring step are particularly advantageous since contrary to standard oxidative hair colouring compositions, these compositions are typically low odour compositions.

In the embodiments wherein in step b) of the hair colouring step, step a) is repeated once, the fourth composition of step a) may comprise one or more second cationic coloured polymer(s) and the fourth composition of the repeated step a) may comprise one or more second cationic uncoloured polymer(s).

The hair colouring step may further comprise step c) of applying after step a) a sixth composition comprising one or more third cationic polymer(s) to a sixth portion of the hair wherein the sixth portion of the hair has at least one common area with the second common area of step a).

Alternatively, the method may further comprise the step d) of applying after step b) a sixth composition comprising one or more third cationic polymer(s) to a sixth portion of the hair, wherein the sixth portion of the hair has at least one common area with the third common area of step b).

In steps c) and/or d), the sixth composition may be applied all over the hair. The third cationic polymer(s) comprised in the sixth composition may be cationic coloured polymers or cationic uncoloured polymers. The third cationic polymer(s) may be selected from the same groups of polymers as described hereinafter for the second cationic polymer(s).

By having a cationic polymeric layer on top of the anionic layer it is possible to provide the user with a good hair feeling which is similar to what is obtained when standard commercially available conditioners are applied to the hair.

Steps $a_1$) and/or $a_2$) of the sequence of steps of the hair colouring step may further comprise the subsequent sub-step of removing the excess of respectively the fourth composition and/or the fifth composition from the hair.

Steps $a_1$) and/or $a_2$) of the sequence of steps of the method may further comprise the subsequent sub-step of applying energy to the hair in the form of heat, ultrasounds, infrared and/or microwaves. This sub-step may be carried out either after the application of the fourth or fifth composition to the hair or after removing the excess of the fourth composition or the fifth composition from the hair. While not wishing to be bound by theory, it is believed that applying energy to the hair may accelerate the speed of formation of the polymeric layers on the hair and therefore may increase the stability of the layers once they are formed on the hair. The hair may be heated to a temperature ranging from 5° C. to 70° C., alternatively 20° C. to 60° C., alternatively 40° C. to 60° C.

Steps $a_1$) and/or $a_2$) of the sequence of steps of the method may further comprise the subsequent sub-step of washing and/or rinsing the hair. The hair may be washed and/or rinsed with a liquid selected from the group consisting of a cosmetically acceptable solvent, a solution comprising a cosmetically acceptable solvent and a cosmetically acceptable salt, a shampoo composition and mixtures thereof. Alternatively, the hair may be washed and/or rinsed with water.

After carrying out the method according to the present invention, a conditioning agent may be applied to the hair. Any of the conditioning agents disclosed hereinafter may be applied to the hair.

Fourth Composition

Pigment(s)

As described hereinbefore, the fourth composition may comprise one or more pigment(s). The pigments are coloured pigments which impart colour effects to the product mass or to the hair, or they may be lustre effect pigments which impart desirable and aesthetically pleasing lustre effects to the composition or to the keratin fibres.

The fourth composition may comprise pigments having a $D_{50}$ particle diameter of from 1 nm to 60 micron. Particle diameter is represented by $D_{50}$, which is the median diameter by volume. $D_{50}$ is measured with a Malvern Mastersizer 2000, which is a laser diffraction particle sizer and it is measured according to ISO 13320:2009(en) with Hydro 2000G or Hydro 2000S where the dispersant is water or ethanol. Detection range is from 0.02 micron to 2000 micron. $D_{50}$ is expressed as $x_{50}$ in ISO 13320:2009(en). Laser diffraction measures particle size distributions by measuring the angular variation in intensity of light scattered as a laser beam passes through a dispersed particulate sample analyser and the particle size is reported as a volume equivalent sphere diameter. A discussion of calculating $D_{50}$ is provided in Barber et al, Pharmaceutical Development and Technology, 3(2), 153-161 (1998), which is incorporated herein by reference.

The fourth composition may comprise pigments having a $D_{50}$ particle diameter of from 100 nm to 20 micron. The pigments may be present in the composition in undissolved form. The fourth composition may comprise a total amount of pigments ranging from 0.01% to 25%, or from 0.1% to 20%, or from 1% to 15%, or from 4% to 10% pigment by total weight of the composition. The pigments are colorants which are virtually insoluble in the composition, and may be inorganic or organic. inorganic-organic mixed pigments are also possible. The fourth composition may comprise inorganic pigments. The advantage of inorganic pigments is their excellent resistance to light, weather and temperature. The inorganic pigments may be of natural origin, and are, for example, derived from material selected from the group consisting of chalk, ochre, umber, green earth, burnt sienna, and graphite. The pigments may be white pigments, such as, for example, titanium dioxide or zinc oxide, or are black pigments, such as, for example, iron oxide black, or are coloured pigments, such as, for example, ultramarine or iron oxide red, lustre pigments, metal effect pigments, pearlescent pigments, and fluorescent or phosphorescent pigments. Alternatively, the pigments may be coloured, non-white pigments. The pigments may be selected from the group consisting of metal oxides, hydroxides and oxide hydrates, mixed phase pigments, sulfur-containing silicates, metal sulfides, complex metal cyanides, metal sulfates, chromates and molybdates, and the metals themselves (bronze pigments). The pigments may be selected from the group consisting of titanium dioxide (CI 77891), black iron oxide (CI 77499), yellow iron oxide (CI 77492), red and brown iron oxide (CI 77491), manganese violet (CI 77742), ultramarine (sodium aluminium sulfosilicates, CI 77007, Pigment Blue 29), chromium oxide hydrate (CI 77289), Prussian blue (ferric ferrocyanide, CI 77510), carmine (cochineal), and mixtures thereof.

The pigments may be pearlescent and coloured pigments based on mica which are coated with a metal oxide or a metal oxychloride, such as titanium dioxide or bismuth oxychloride, and optionally further colour-imparting substances, such as iron oxides, Prussian blue, ultramarine, and carmine. The colour exhibited by the pigment can be adjusted by varying the layer thickness. Such pigments are sold, for example, under the trade names Rona®, Colorona®, Dichrona®, RonaFlair®, Ronastar®, Xirona® and Timiron® all of which are available from Merck, Darmstadt, Germany. For example, Xirona® is a brand for colour travel pigments that display colour shifting effects depending on the viewing angle and are based on either natural mica, $SiO_2$ or calcium aluminium borosilicate flakes, coated with varying layers of $TiO_2$. Pigments from the line KTZ® from Kobo Products, Inc., 3474 So. Clinton Ave., So. Plainfield, USA, are also useful herein, in particular the Surface Treated KTZ® Pearlescent Pigments from Kobo. Particularly useful are KTZ® FINE WHITE (mica and $TiO_2$) having a $D_{50}$ particle diameter of 5 to 25 micron and also KTZ® CELESTIAL LUSTER (mica and $TiO_2$, 10 to 60 micron) as well as KTZ® CLASSIC WHITE (mica and $TiO_2$, 10 to 60 micron). Also useful are SynCrystal Sapphire from Eckart Effect Pigments, which is a blue powder comprising platelets of synthetic fluorphlogopite coated with titanium dioxide, ferric ferrocyanide and small amounts of tin oxide. Also useful is SYNCRYSTAL Almond also from Eckart, which is a beige powder with a copper reflection colour and is composed of platelets of synthetic fluorphlogopite and coated with titanium dioxide and iron oxides. Also useful is Duocrome® RV 524C from BASF, which provides a two colour look via a lustrous red powder with a violet reflection powder due to its composition of mica, titanium dioxide and carmine.

The pigments may be organic pigments. The organic pigments may be selected from the group consisting of natural pigments sepia, gamboge, bone charcoal, Cassel brown, indigo, chlorophyll and other plant pigments. The synthetic organic pigments may be selected from the group consisting of azo pigments, anthraquinoids, indigoids, dioxazine, quinacridone, phthalocyanine, isoindolinone, perylene and perinone, metal complex, alkali blue, diketopyrrolopyrrole pigments, and combinations thereof.

The pigments may be selected from the group consisting of iron oxide, titanium dioxide, mica, borosilicate, and combinations thereof. The pigments may comprise an iron oxide ($Fe_2O_3$) pigment. The pigment may comprise a combination of mica and titanium dioxide.

Second Cationic Polymer(s)

As explained hereinbefore, the fourth composition may comprise one or more second cationic polymer(s). The second cationic polymer(s) may be selected from the group consisting of cationic coloured polymers, cationic uncoloured polymers and mixtures thereof.

Each of the second cationic polymers which are comprised in each of the fourth compositions of step a) and of the repeated steps a) may be the same or different.

In step a) and/or in each of the repeated steps a), the second cationic polymer(s) may be cationic coloured polymers.

The second cationic polymer(s) according to the present invention may comprise one or more monomer unit(s) comprising one or more amino functional group(s). The amino functional group(s) may be selected from the group consisting of primary, secondary, tertiary, quaternary amino functional groups and mixtures thereof The amino functional group(s) may preferably be selected from the group consisting of primary, secondary amino functional groups and mixtures thereof. The amino functional group(s) may more preferably be selected from secondary amino functional groups.

The second cationic polymer(s) may have a charge density at full protonation of at least 0.3, preferably at least 0.6, more preferably at least 0.8, even more preferably at least 1.0 positive charges per monomer unit.

The second cationic polymer(s) may have a weight average molecular weight of more than 0.5 kD, preferably from 0.5 kD to 5000 kD, more preferably from 2 kD to 1000 kD, even more preferably from 10 kD to 200 kD, most preferably from 25 kD to 70 kD.

The second cationic polymer(s) may be selected from the group consisting of polyethyleneimine, polyallylamine hydrochloride, poly vinyl amine, polydiallyldimethylammonium chloride, copolymers thereof and mixtures thereof.

The copolymers may be random or block copolymers.

The second cationic polymer(s) may be linear or branched.

The second cationic polymer(s) may be selected from the group consisting of:

a) Linear polyethyleneimine of the formula:

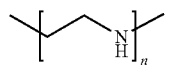

in which n is an integer representing the degree of polymerization, wherein n ranges from 50 to 20,000, alternatively from 100 to 3,500;

b) Branched polyethyleneimine consisting of primary, secondary and tertiary amine groups of the formula:

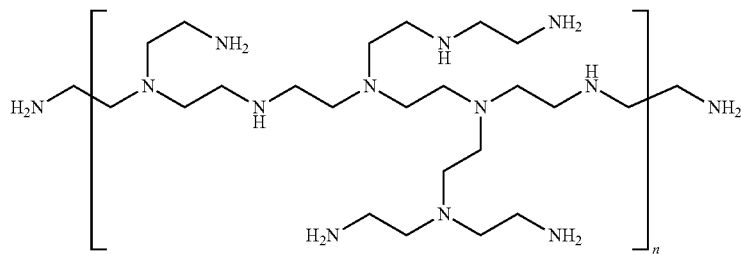

in which n is an integer representing the degree of polymerization, wherein n ranges from 5 to 4,000, alternatively from 50 to 500;

c) Polyallylamine hydrochloride (PAH) of the formula:

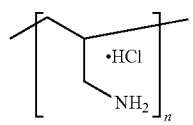

in which n is an integer representing the degree of polymerization, wherein n ranges from 50 to 20,000, alternatively from 150 to 2000;

d) Polydiallyldimethylammonium chloride (PDADMAC) of the formula:

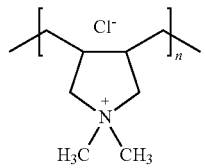

in which n is an integer representing the degree of polymerization, wherein n ranges from 10 to 20,000, alternatively from 150 to 4,000; copolymers thereof and mixtures thereof.

The copolymers may be random or block copolymers,

The fourth composition may be the same composition as the first composition. The fourth composition may comprise the same cationic polymers as the ones comprised in the first composition.

Fifth Composition

Second Anionic Polymer(s)

The second anionic polymer(s) which are comprised in the fifth composition may be selected from the group consisting of anionic coloured polymers, anionic uncoloured polymers and mixtures thereof.

Each of the second anionic polymer(s) which are comprised in each of the fifth compositions of step a) and of the repeated steps a) may be the same or different.

In step a) and/or in each of the repeated steps a), the second anionic polymer(s) may be anionic coloured polymers.

The second anionic polymer(s) may have a charge density at full deprotonation of at least 0.3, preferably at least 0.6, more preferably at least 0.8, even more preferably at least 1.0 negative charges per monomer unit.

The second anionic polymer(s) may have a weight average molecular weight of at least 1 kD, preferably from 10 kD to 1000 kD, more preferably from 70 kD to 500 kD.

The second anionic polymer(s) may comprise one or more monomer unit(s) comprising one or more functional group(s) selected from the group consisting of sulfate, sulfonate, carboxylate, phosphate, phosphonate groups and mixtures thereof. The functional group(s) may preferably be selected from the group consisting of sulfate, sulfonate, carboxylate groups and mixtures thereof.

The second anionic polymer(s) may be selected from the group consisting of polystyrene sulfonate salts, λ-carrageenan salts, dextran sulfate salts, polyacrylic acid salts, poly(methacrylic acid) salts, alginic acid salts, carboxymethylcellulose salts, polystyrene sulfonate/polystyrene copolymer salts, copolymers thereof and mixtures thereof. The salts may be sodium salts.

The copolymers may be random or block copolymers.

The second anionic polymer(s) may be selected from the group consisting of:

a) Polystyrene sulfonate (PSS) sodium salt of the formula:

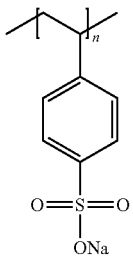

in which n is an integer representing the degree of polymerization, wherein n ranges from 50 to 20,000, alternatively from 150 to 500;

b) Co-polymer of polystyrene sulfonate (PSS) sodium salt and poly(4-styrenesulfonic acid-co-maleic acid) of the formula:

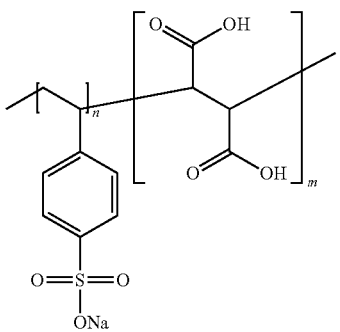

in which n and m are integers representing the degree of polymerization, wherein n+m ranges from 50 to 20,000, alternatively from 150 to 2500;

c) λ-Carrageenan;

d) Dextran sulfate sodium salt;

e) Polyacrylic acid (PAA) of the formula:

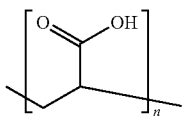

in which n is an integer representing the degree of polymerization, wherein n ranges from 50 to 20,000, alternatively from 150 to 5000;

f) Alginic acid sodium salt;

g) Carboxymethylcellulose sodium salt of the formula:

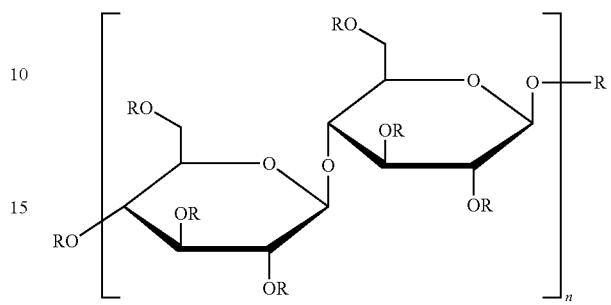

in which:

R is H or $(CH_2)_2COONa$ and n is an integer representing the degree of polymerization; copolymers thereof and mixtures thereof.

The copolymers may be random or block copolymers.

The fifth composition may be the same as the second composition. The fifth composition may comprise the same anionic polymers as the ones comprised in the second composition.

Cationic Coloured Polymers and Anionic Coloured Polymers

The cationic coloured polymers and the anionic coloured polymers used in the present invention comprise at least one chromophore and/or at least one fluorophore. Any of the hereinbefore exemplified cationic polymers or anionic polymers can comprise at least one chromophore and/or at least one fluorophore either in the skeleton or as pendent group.

The chromophores may be selected from the group consisting of nitrobenzene, azo, imine, hydrazine, phenothiazine, xanthene, phenanthridine, phthalocyanin and triarylmethane-based dyes, derivatives thereof, derivatives obtained from direct dyes containing a carbonyl group and mixtures thereof. The chromophores may be selected from the group consisting of acridone benzoquinone, anthraquinone, naphthoquinone, benzanthrone, anthranthrone, pyranthrone, pyrazolanthrone, pyrimidinoanthrone, flavanthrone, indanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin dyes, derivatives thereof and mixtures thereof.

The chromophores may be substituted with at least one amine, hydroxyl, sulfate, sulfonate, carboxylate, phosphate, phosphonate, or halide group. These chromophores may be selected from the group consisting of derivatives of acidic nitro direct dyes, acidic azo dyes, acidic azine dyes, acidic triarylmethane dyes, acidic indoamine dyes and non-quinone acidic natural dyes, and mixtures thereof.

The chromophores may also be selected from derivatives of any of the direct dyes exemplified in the direct dyes section of this application.

The fluorophores may be selected from the group consisting of derivatives from di-, tetra- or hexa-sulfonated triazine-stilbenes, coumarins, imidazolines, diazoles, triazoles, benzoxazolines, biphenyl-stilbenes optical brighteners, and mixtures thereof.

A cationic coloured polymer or an anionic coloured polymer may comprise the same type of chromophore and/or fluorophore or different types of chromophores and/or fluorophores. Having a cationic coloured polymer or an anionic coloured polymer with different types of chromophores and/or fluorophores may help to cover a broad range of colour shades which can be obtained on hair which are coloured according to the method of the present wherein the first composition or the second composition comprises such a cationic coloured polymer or such an anionic coloured polymer.

The cationic coloured polymers may be selected from the group consisting of:

i. Coloured linear or branched polyethyleneimine (PEI) of the formula:

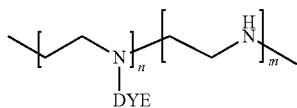

in which n and m are integers representing the degree of polymerization, wherein m/n ranges from 0 to 1,000 provided that n is different from 0 and/or m+n ranges from 50 to 20,000, alternatively from 100 to 3,500;

ii. Coloured polyallylamine of the formula:

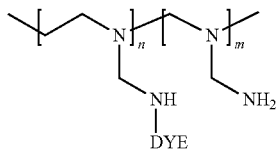

in which n and m are integers representing the degree of polymerization, wherein m/n ranges from 0 to 1,000 provided that n is different from 0 and/or m+n ranges from 50 to 20,000, alternatively from 150 to 2000;

iii. Coloured polydiallyldimethylammonium chloride of the formula:

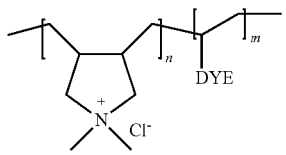

in which n and m are integers representing the degree of polymerization, wherein m/n ranges from 0 to 1,000 provided that n is different from 0 and/or m+n ranges from 10 to 20,000, alternatively from 100 to 4000;

wherein DYE represents the chromophore or the fluorophore that is attached to the polymer skeleton either directly or via a saturated or unsaturated, linear or branched hydrocarbon-based chain containing from 1 to 10 carbon atoms or from 1 to 6 carbon atoms. These polymers may be block copolymers or random copolymers.

The cationic coloured polymers may be selected from linear polyethyleneimine (PEI)—Rhodamine B of the formula:

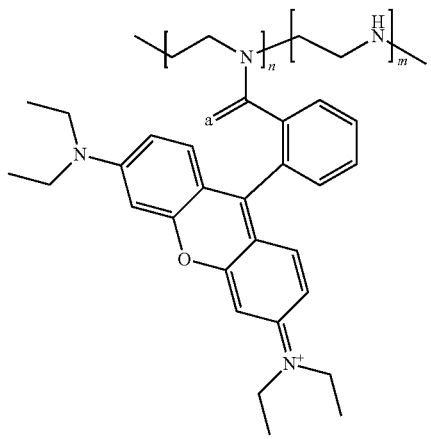

in which n and m are integers representing the degree of polymerization, wherein m/n may range from 0 to 1,000 provided that n is different from 0 and/or m+n may range from 50 to 20,000, alternatively from 100 to 3,500. These polymers may be block copolymers or random copolymers.

The anionic coloured polymers may be selected from anionic coloured polymers with the following formula:

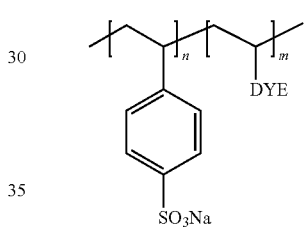

in which n and m are integers representing the degree of polymerization, wherein m/n may range from 0 to 1,000 provided that n is different from 0 and/or m+n may range from 50 to 20,000, alternatively from 150 to 500;

wherein DYE represents the chromophore or the fluorophore that is attached to the polymer skeleton either directly or via a saturated or unsaturated, linear or branched hydrocarbon-based chain containing from 1 to 10 carbon atoms or from 1 to 6 carbon atoms. These polymers may be block copolymers or random copolymers.

First to Sixth Compositions

Solvents

The first to sixth compositions which are used to carry out the method according the present invention may further comprise at least one solvent. The solvent may be selected from water, or a mixture of water and at least one organic solvent to dissolve the compounds that would not typically be sufficiently soluble in water. The first to sixth compositions may be aqueous solutions.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

The solvent may be selected from the group consisting of water, ethanol, propanol, isopropanol, glycerol, 1,2-propylene glycol, hexylene glycol, ethoxy diglycol, and mixtures thereof.

Typically, the compositions may comprise water as a main ingredient, particularly in a total amount ranging from at least 50%, alternatively from at least 60%, alternatively from at least 70%, by total weight of the composition. Typically, when present, the compositions comprise a total amount of organic solvents ranging from about 1% to about 30%, by total weight of the composition.

Concentrations

The first and/or the fourth composition may comprise a total concentration of cationic polymers which is ranging from 0.1 g/L to 100 g/L, alternatively from 0.5 g/L to 100 g/L, alternatively from 2g/L to 50 g/L, alternatively from 5 g/L to 10 g/L.

The second and/or the fifth composition may comprise a total concentration of anionic polymers which is ranging from 0.1 g/L to 100 g/L, alternatively from 0.5 g/L to 100 g/L, alternatively from 2g/L to 50 g/L, alternatively from 5 g/L to 10 g/L.

Salt

The first to sixth compositions may comprise at least one cosmetically acceptable salt at a concentration ranging from 0 to 1.5 mol/L, preferably from 0.05 to 1 mol/L, more preferably from 0.2 to 0.5 mol/L.

The cosmetically acceptable salt may be selected from the group consisting of an organic salt, a mineral salt and mixture thereof. The organic salt may be sodium citrate. The mineral salt may be selected from the group consisting of sodium chloride, ammonium sulfate, magnesium chloride, calcium chloride and mixtures thereof. The cosmetically acceptable salt may be sodium chloride.

Applicators

The first to sixth compositions may be applied to the hair using an applicator such as a brush or a sponge. Alternatively, the first to sixth composition may be applied to the hair by spraying or foaming the first to sixth composition to the hair or by dipping the hair into the first to sixth composition. Alternatively, the first to sixth composition may be applied to the hair using printing technology.

Hair Colouring Kit

The present invention also relates to a kit for treating hair comprising a first component comprising the first composition as defined hereinbefore, a second component comprising the second composition as defined hereinbefore and a third component comprising the third composition as defined hereinbefore. The kit may further comprise a fourth component comprising the fourth composition as defined hereinbefore and/or a fifth component comprising the fifth composition as defined hereinbefore.

Other Ingredients

The first to sixth compositions according to the present invention may comprise, in addition to the ingredients indicated above, further ingredients in order to further enhance the properties of the composition, as long as these are not excluded by the claims.

Suitable further ingredients include, but not limited to: alkalizing agents; oxidative dye precursors, direct dyes; chelants; radical scavengers; pH modifiers and buffering agents; thickeners and/or rheology modifiers; carbonate ion sources; peroxymonocarbonate ion sources; surfactants; polymers; fragrances; enzymes; dispersing agents; peroxide stabilizing agents; antioxidants; natural ingredients (such as proteins, protein compounds, and plant extracts); conditioning agents (such as silicones and cationic polymers); cer-amides; preserving agents; opacifiers and pearling agents (such as titanium dioxide and mica); and mixtures thereof.

Suitable further ingredients referred to above, but not specifically described below, are listed in the International Cosmetics Ingredient Dictionary and Handbook. (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Alkalizing Agents

The first to sixth compositions according to the present invention may further comprise at least one alkalizing agent. Any alkalizing agent known in the art may be used.

Typically, the first to sixth compositions may comprise a total amount of alkalizing agents ranging from 0.1% to 10%, alternatively from 0.5% to 6%, alternatively from 1% to 4%, by total weight of the composition.

Alternatively, the first to sixth compositions may comprise a total amount of alkalizing agents of less than 1%, preferably less than 0.5%, more preferably less than 0.3%, even more preferably less than 0.1% by total weight of the composition. Suitable alkalizing agents include, but are not limited to: ammonia; alkanolamines (such as monoethanolamine, diethanolamine, triethanolamine, monopropanolamine, dipropanolamine, tripropanolamine 2-amino-2-methyl-1,3-propanediol, 2-amino-2-methyl-1-propanol, and 2-amino-2-hydroxymethyl-1,3-propanediol); guanidium salts; alkali metal and ammonium hydroxides (such as sodium hydroxide); alkali metal and ammonium carbonates; and mixtures thereof. Typical alkalizing agents are ammonia and/or monoethanolamine.

The first to sixth compositions may comprise a total amount of ammonia of less than 1%, preferably less than 0.5%, more preferably less than 0.3%, even more preferably less than 0.1% by total weight of the composition. The first to sixth compositions may most preferably be free of ammonia. These embodiments are particularly interesting since such compositions are low odour compositions.

Preferably, if present, the ammonium ions and carbonate ions are present in the composition at a weight ratio of from 3:1 to 1:10, alternatively from 2:1 to 1:5.

When the compositions of the present invention is obtained by mixing a developer and a tint composition prior to use, the alkalizing agent is generally present in the tint composition.

Oxidative Dye Precursors

The first to sixth compositions according to the present invention may further comprise oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Typically, the first to sixth compositions may comprise a total amount of oxidative dye precursors ranging up to 12%, preferably from 0.1% to 10%, more preferably from 0.3% to 8%, even more preferably from 0.5% to 6%, by total weight of the composition.

Suitable primary intermediates include, but are not limited to: toluene-2,5-diamine, p-phenylenediamine, N-phenyl-p-phenylenediamine N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino) ethylazanediyl)diethanol, 2-(2,5-diamino-4-methoxyphenyl)propane-1,3-diol, -(7-amino-2H-benzo[b][1,4]oxazin-4 (3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5, 6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy] ethanol hydrochloride, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethlaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy) diethanol, 3-(pyrrolidin-1-yl)aniline, 1-(3-(dimethylamino) phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy -3,4-dimethypyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

When the compositions of the invention are obtained by mixing a tint composition and a developer composition, the primary intermediates and couplers are usually incorporated into the tint composition.

Direct Dyes

The first to sixth compositions according to the present invention may further comprise compatible direct dyes, in an amount sufficient to provide additional colouring, particularly with regard to intensity. Typically, the first to sixth compositions may comprise a total amount of direct dyes ranging from about 0.05% to about 4%, by total weight of the composition.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl) (ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No.2, HC Yellow No. 4, HC Yellow No. 2, HC Orange No. 1, HC Red No. 1, 2-(4-amino-2-chloro-5-nitrophenylamino)ethanol, HC Red No. 3,4-amino-3-nitrophenol, 4-(2-hydroxyethylamino)-3-nitrophenol, 2-amino-3-nitrophenol, 2-(3-(methylamino)-4-nitrophenoxy)ethanol 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12. HC Blue No. 10, HC Yellow No. 7, HC Yellow No. 10, HC Blue No. 9,2-chloro-6-(ethylamino)-4-nitrophenol, 6-nitropyridine-2, 5-diamine, HC Violet No. 2,2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No, 15, HC Yellow No. 14, N2-methyl-6-nitropyridine-2,5-diamine, N1-allyl-2-nitrobenzene-1,4-diamine, HC Red No. 8, HC Green No.1, HC Blue No. 14; Natural dyes such as Annato, Anthocyanin, Beetroot, Carotene, Capsanthin, Lycopene, Chlorophyll, Henna, Indigo, Cochineal; and mixtures thereof.

When the compositions are obtained by mixing a tint composition and a developer composition, the direct dyes are usually incorporated into the tint composition.

Chelants

The first to sixth compositions according to the present invention may further comprise at least one chelant (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell &. R M Smith, Critical Stability Constants, Vol. 1, Plenum Press, New York & London (1974) and A E Martell & R D Hancock, Metal Complexes in Aqueous Solution, Plenum Press, New York & London (1996), both incorporated herein by reference.

Typically, the first to sixth compositions may comprise a total amount of chelants ranging from at least 0.01%, preferably from 0.01% to 5%, more preferably from 0.25% to 3%, even more preferably from 0.5% to 1%, by total weight of the composition.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof By "salts thereof", it is meant in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof.

Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N-N'-diglutaric acid (EDDG), 2-hydroxypropylenediamine-N-N'-disuccinic acid (HPDDS), ethylenediaminetetraacetic acid (EDTA), ethylenedicysteic acid (EDC), ethylenediamine-N-N'-bis(ortho-hydroxyphenyl acetic acid) (EDDHA), diaminoalkyldi(sulfosuccinic acids) (DDS), N,N'-bis(2-hydroxybenzypethylenediamine-N,N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof; their derivatives thereof, and mixtures thereof.

Suitable aminophosphonic acid chelants comprise an aminophosphonic acid moiety (—$PO_3H_2$) or its derivative—$PO_3R_2$, wherein $R_2$ is a $C_1$ to $C_6$ alkyl or aryl group and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylene-diaminetetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N"-ethylenediamine diacetic acid, their salts thereof, their derivatives thereof, and mixtures thereof.

In a specific embodiment, the composition comprises a chelant selected from the group consisting of diethylenetriamine-N,N',N"-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

When the compositions of the invention are obtained by mixing a tint composition and a developer composition, the chelants may be incorporated in the tint composition and/or in the developer composition. A chelant is usually present in the developer composition for stability reason.

Radical Scavengers

The first to sixth compositions according to the present invention may further comprise at least one radical scavenger. As used herein the term "radical scavenger" refers to a species that can react with a radical, preferably a carbonate radical to convert the radical species by a series of fast reactions to a less reactive species. In one embodiment, the radical scavenger is different from the alkalising agent and/or is present in an amount sufficient to reduce the damage to the hair during the colouring/bleaching process.

Typically, the first to sixth compositions may comprise a total amount of radical scavengers ranging from 0.1% to 10%, preferably from 1% by weight to 7%, by total weight of the composition.

Suitable radical scavengers include, but are not limited to: alkanolamines, amino sugars, amino acids, esters of amino acids, and mixtures thereof; alternatively 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, their salts thereof and mixtures thereof alternatively glycine, sarcosine, lysine, serine, 2 methoxyethylamine, glucosamine, glutamic acid, morpholine, piperdine, ethyl amine, 3 amino-1-propanol, and mixtures thereof. As used herein, the term "salts thereof"—in the context of radical scavengers—means particularly potassium salts, sodium salts, ammonium salts, and mixtures thereof.

pH Modifiers and Buffering Agents

The first to sixth compositions according to the present invention may further comprise, in addition to the alkalizing agent discussed above, a pH modifier and/or buffering agent.

Suitable pH modifiers and/or buffering agents include, but are not limited to: ammonia; alkanolamines (such as monoethanolamine diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifiers and/or buffering agents include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

Thickeners and/or Rheology Modifiers

The first to sixth compositions according to the invention may further comprise at least one thickener in an amount sufficient to provide the compositions with a viscosity so that it can be readily applied to the hair without unduly dripping off the hair and causing mess.

Typically, the first to sixth compositions may comprise a total amount of thickeners ranging from at least 0.1%, preferably at least 0.5%, more preferably at least 1%, by total weight of the composition.

Suitable thickeners include, but are not limited to: associative polymers, polysaccharides, non-associative polycarboxylic polymers, and mixtures thereof.

Carbonate Ion Sources

The first to sixth compositions according to the present invention may further comprise at least one source of carbonate ions, carbamate ions, hydrogen carbonate ions, and mixtures thereof in a sufficient amount to reduce damage to the hair during the colouring process.

Typically, the first to sixth compositions may comprise a total amount of a carbonate ion source ranging from 0.1% to 15%, preferably from 0.1% to 10%, more preferably from 1% to 7%, by total weight of the composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof; alternatively ammonium carbonate, ammonium hydrogen carbonate, and mixtures thereof.

Conditioning Agents

The first to sixth compositions according to the present invention may further comprise at least one conditioning agent, and/or be used in combination with a composition comprising at least one conditioning agent.

Typically, the first to sixth compositions may comprise a total amount of conditioning agents ranging from 0.05% to 20%, preferably from 0.1% to 15%, more preferably from 0.2% to 10%, even more preferably from 0.2% to 2%, most preferably from 0.5% to 2%, by total weight of the composition. The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol.

Surfactant(s)

The first, second, fourth, fifth or sixth composition according to the present invention may further comprise one or more surfactant(s).

Typically, the first, second, fourth, fifth or sixth composition may comprise a total amount of surfactants ranging from 0.1% to 30%, preferably from 2% to 30%, more preferably from 8% to 25%, even more preferably from 10% to 20%, by total weight of the composition.

The first, second, fourth, fifth or sixth composition may comprise one or more surfactant(s) selected from the group consisting of anionic surfactants, amphoteric surfactants, nonionic surfactants and mixtures thereof. The first, second, fourth, fifth or sixth composition may comprise a total amount of anionic surfactants ranging from 0.1% to 20%, preferably from 0.1% to 15%, more preferably from 5% to 15%, by total weight of the compositions; and a total amount of amphoteric and/or nonionic components, which may range independently from each other from 0.1% to 15%, preferably from 0.5% to 10%, more preferably from 1% to 8%, by total weight of the compositions.

Ionic Strength

The first to sixth compositions of the present invention may further have an ionic strength as defined herein of less than 1.35 mole/kg, preferably from 0.10 to 0.75 mole/kg, more preferably from 0.20 to 0.60 mole/kg. Whilst not being bound by theory, it is believed that the ionic strength value may also affect the resultant viscosity and root adhesion properties of the composition. The ionic strength can be affected by salt resources such as the dyes, sodium sulphate, ammonium carbonate anti-oxidants and chelants such as EDDS. The dye tends to have the greatest effect on the ionic strength and thus the amounts added in order to provide any particular shade need to be considered in terms of ionic strength as well as dye outcome in order to prevent viscosity and root adhesion problems.

The ionic strength of the compositions is a function of the concentration of all ions present in that solution and is determined according to the formula:

$$I = \frac{1}{2}\sum_{i=1}^{n} m_i z_i^2$$

where $m_i$=molality of ion i (M=mol·/Kg $H_2O$), $z_i$=charge number of that ion, and the sum is taken over all ions in the solution. For example, for a 1:1 electrolyte such as sodium chloride, the ionic strength is equal to the concentration, but for $MgSO_4$ the ionic strength is four times higher. Generally multivalent ions contribute strongly to the ionic strength.

For example the ionic strength of a mixed 0.050 M $Na_2SO_4$ and 0.020 M NaCl solution is: $I=\frac{1}{2}((2\times(+1)^2\times 0.050)+(+1)^2\times 0.020+(-2)^2\times 0.050+(-1)^2\times 0.020)=0.17$ M.

Foam

The first to sixth compositions of the invention may be provided in the form of foam which is applied to the hair. Foam formation is typically achieved by the use of a foaming agent incorporated within the composition in combination with a manually operated foaming device. Such manually operated foaming devices are known in the art and include aerosols devices, squeeze foamers and pump foamers.

Suitable foaming agents includes surfactants such as anionic, nonionic and amphoteric surfactants, nonionic surfactants being preferred; polysaccharides; polyvinyl pyrrolidone and copolymers thereof; acrylic polymers such as Acrylates copolymer (Aculyn 33) and Acrylates/Steareth-20 methacrylates (Aculyn 22); C12-C24 fatty acids such as stearates and mixtures thereof.

EXAMPLES

The following are non-limiting examples of the method of the present invention. The examples are given solely for the purpose of illustration and are not to be construed as limitations of the present invention, as many variations thereof are possible without departing from the spirit and scope of the invention, which would be recognized by one of ordinary skill in the art.

In the following section the solvent used to prepare the different compositions is water, unless otherwise specified.

Synthesis Methods for Obtaining the Different Cationic or Anionic Coloured Polymers Used in the Examples:

Cationic Coloured Polymers

Branched polyethyleneimine labeled with Reactive Red 180 (PEI-Red):

Starting materials:
  Branched polyethyleneimine (PEI) (LUPASOL G 500), Mw=25,000 Da, available from BASF (CAS: 90(2-98-6)
  Reactive Red 180 available from S3 Chemicals (CAS: 72828-03-6).

Synthesis Method:

The following method has been used for labeling Branched polyethyleneimine (PEI) with Reactive Red 180 (Red):

1) Dissolving 12.5 g of a 40 wt % solution of Branched polyethyleneimine (PEI) in a 200 ml methanol solution containing 14.05 g of Reactive Red 180;

2) Stirring the suspension at 60° C. for 1 hour;
3) Further stirring the resultant mixture at room temperature for 12 h;
4) Centrifuging the resultant mixture and collecting the supernatant;
5) Adding methanol to the precipitate, centrifuging the mixture and collecting the supernatant;
6) Repeating step 5) until the resulting supernatant is colorless;
7) Mixing all the resulting supernatant solutions from steps 4) to 6);
8) Adding 12.5 ml of a 32 wt % hydrochloric acid solution to the resulting mixture from step 7)
9) Centrifuging the resulting suspension and collecting the precipitate;
10) Washing the precipitate with acetone until the supernatant is colorless;
11) Drying the precipitate and dissolving it in water;
12) Dialyzing the resulting solution against a solution of 0.15 M NaCl and $10^{-4}$ to $10^{-5}$ M HCl
13) Freeze-drying the product Branched polyethyleneimine (PEI) Labeled with Remazol Brilliant Blue R (PEI-Blue):
Starting Materials:
Branched polyethyleneimine (PEI), LUPASOL G 500, Mw=25,000 Da (CAS: 9002-98-6) available from BASF
Remazol brilliant Blue R available from Sigma-Aldrich (CAS: 2580-78-1)
Synthesis Method:
The same method as for labeling Branched polyethyleneimine with Reactive Red 180 has been used wherein Reactive Red 180 was replaced by Remazol brilliant Blue R and wherein in step 1) 12.5 g of a 40 wt % Branched polyethyleneimine (PEI) solution were dissolved in a 200 ml methanol solution containing 7.3 g of Remazol brilliant Blue R.

Polydiallyldimethylammonium Chloride Copolymerized with Methacryloxyethyl Thiocarbamoyl Rhodamine B (PDADMAC-Red):
Starting Materials:
Monomeric diallyldimethylammonium chloride (CAS. 7398-69-8) available from Sigma-Aldrich
Methacryloxyethyl thiocarbamoyl rhodamine B (RhoB), available from Polysciences
Synthesis Method:
1.61 g monomeric diallyldimethylammonium chloride and 33 mg methacryloxyethyl thiocarbamoyl rhodamine B were copolymerized in 20 mL 50% methanol at 80° C. under nitrogen atmosphere for 24 hours using 10 mg potassium peroxodisulfate as initiator. After polymerization, the coloured polymer was dialyzed against distilled water.

Anionic Coloured Polymers
Polystyrene sulfonate copolymerized with Rhodamine B isothiocyanate (PSS-Red):
Starting Materials:
Monomeric Sodium 4-vinylbenzenesulfonate (CAS: 2695-37-6) available from Sigma-Aldrich.
Methacryloxyethyl thiocarbamoyl rhodamine B (RhoB), available from Polysciences
Synthesis Method:
The same method as for copolymerizing Polydiallyldimethylammonium chloride with Methacryloxyethyl thiocarbamoyl rhodamine B has been used wherein 1.61 g monomeric diallyldimethylammonium chloride has been replaced by 2.05 g monomeric Sodium 4-vinylbenzenesulfonate.

Cationic Uncoloured Polymer Used in the Examples
Polydiallyldimethylammonium chloride (PDADMAC), Mw=100,000-200,000 Da (CAS:26062-79-3) available from Sigma-Aldrich
Branched polyethyleneimine (PEI), LUPASOL G 500, Mw=25,000 Da (CAS: 9002-98-6) available from BASF
Polyallylamine hydrochloride (PAH), Mw=15,000 Da (CAS: 71550-12-4) available from Sigma-Aldrich
Anionic Uncoloured Polymer Used in the Examples
Dextran sulfate sodium salt (DxS), Mw=500,000 Da (CAS: 9011-18-1) available from Fluka.
Poly(acrylic) acid sodium salt (PAA), Mw=30,000 Da (CAS: 9003-04-7) available from Aldrich
Poly(methacrylic acid) sodium salt (PIMA), Mw:=15,000 Da (CAS: 25087-26-7) available from Polysciences, Inc.
Alginic acid sodium salt (CAS: 9005-38-3) available from Fluka
Polystyrene sulfonate sodium salt (PSS), Mw=70,000 Da (CAS: 25704-18-1) available from Sigma-Aldrich.
Polystyrene sulfonate/polystyrene copolymer sodium salt (PSS-PS). Mw=30,000-50,000 Da (CAS: 31619-79-1) available from Tosoh Organic Chemical CO. LTD The hair swatches which have been used in the following sets of experimental data are natural hair blond hair swatches available from Kerling International Haarfabrik GmbH, Backnang, Germany with the reference number 826533.

Surfactants Used in the Examples
Cetrimonium bromide (CTAB) (CAS: 57-09-09) available from Fluka
Dodecyltrimethylammonium bromide (DoTAB) (CAS: 1119-94-4) available from Abcr
Tetradecyltrimethylammonium bromide (TTAB) (CAS: 1119-97-7) available from Sigma-Aldrich
Sodium lauryl sulfate (SLS) available from Sigma-Aldrich
Polysorbate 20 available from Sigma-Aldrich wider the tradename Tween 20

First Set of Experimental Data—Examples of Methods According to the Present Invention wherein Different Types of Surfactants have been Used in the Third Composition Example 1A

| First Composition | |
|---|---|
| Ingredients | g/l |
| PDADMAC | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

| Second or Fifth Composition | |
|---|---|
| Ingredients | g/l |
| PSS | 5.00 (0.5 wt %) |
| NaCl | 11.69 (0.2 mol/l) |

-continued

| Second or Fifth Composition | |
|---|---|
| Ingredients | g/l |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

| Fourth Composition | |
|---|---|
| Ingredients | g/l |
| PEI-Red | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5%) | pH adjusted to 8 by adding 1.0 mol/l NaOH or 1.0 mol/l HCl

| Third Composition | |
|---|---|
| Ingredients | g/l |
| CTAB | 18.22 (0.05 mol/l) | pH was not adjusted

Step 1: Formation of the First Polymeric Layer and the Coloured Layer on Top of the First Polymeric Layer:

A hair swatch has been treated according to the following protocol:
(i) Preparing the first, second, fourth and fifth compositions shortly before application;
(ii) Applying 4 mL of the first composition to the hair swatch with a brush and wrapping the hair swatch with a commercial kitchen plastic wrap;
(iii) Agitating the first composition with the hair swatch in plastic wrap for 15 min at 55° C. in a laboratory-type drying cabinet;
(iv) Rinsing the hair swatch for 30 s with running lukewarm tap water at a temperature of 30° C. to 35° C.;
(v) Applying 4 mL of the second composition to the hair swatch with a brush and wrapping the hair swatch with a commercial kitchen plastic wrap;
(vi) Agitating the second composition with the hair swatch in plastic wrap for 15 min at 55° C. in a laboratory-type drying cabinet;
(vii) Rinsing the hair swatch for 30 s with running lukewarm tap water at a temperature of 30° C. to 35° C.;
(viii) Applying 4 mL of the fourth composition to the hair swatch with a brush and wrapping the hair swatch with a commercial kitchen plastic wrap;
(ix) Agitating the fourth composition with the hair swatch in plastic wrap for 15 min at 55° C. in a laboratory-type drying cabinet;
(x) Rinsing the hair swatch for 30 s with running lukewarm tap water at a temperature of 30° C. to 35° C.;
(xi) Applying 4 mL of the fifth composition to the hair swatch with a brush and wrapping the hair swatch with a commercial kitchen plastic wrap;
(xii) Agitating the fifth composition with the hair swatch in plastic wrap for 15 min at 55° C. in a laboratory-type drying cabinet;
(xiii) Rinsing the hair swatch for 30 s with running lukewarm tap water at a temperature of 30° C. to 35° C.;
(xiv) Drying the hair swatch first with tissue paper and then with a hair dryer.

Step 2: Removal of the First Polymeric Layer

The hair swatch obtained at the end of step 1) has been then treated according to the following protocol:
(i) Applying 5ml of the third composition to the coloured hair swatch with a brush for 30 s in a plastic bowl and letting the hair swatch soaked for 30 s;
(ii) Rinsing the hair swatch for 30 s with running lukewarm tap water at a temperature of 30° C. to 35° C.;
(iii) Drying the hair swatch first with tissue paper and then with a hair dryer.

Comparative Example 1A

A hair swatch has been treated as in example 1A except that the third composition has been replaced with the following third composition:

| Third Composition | |
|---|---|
| Ingredients | g/l |
| Sodium dodecyl sulfate (SLS) | 14.42 (0.05 mol/l) | pH was not adjusted

Comparative Example 2A

A hair swatch has been treated as in example 1A except that the third composition has been replaced with the following third composition:

| Third Composition | |
|---|---|
| Ingredients | g/l |
| Polysorbate 20 | 61.38 (0.05 mol/l) | pH was not adjusted

Comparative Example 3A

A hair swatch has been treated as in example 1A except that the third composition has been replaced with water.

L*, b* Measurements

The colorimetric parameters in the CIE L* a* b* system have been measured for each of the hair swatches obtained in Example 1A and comparative examples 1A and 2A using a Minolta CM-508i spectrophotometer (illuminant is D65 daylight with 10° observer) in which L* represents the lightness of the colour, a* indicates the green/red colour axis and b* the blue/yellow colour axis at three different stages:
Stage 1: Before the hair swatch has been treated according to step 1)
Stage 2: After the hair swatch has been treated according to step 1) and before the hair swatch has been treated according to step 2)
Stage 3: After the hair swatch has been treated according to step 2)

Overall color change is represented by ΔE where ΔE is defined by the following formula:

$$\Delta E=[(\Delta L^*)^2+(\Delta a^*)^2+(\Delta b^*)^2]^{1/2}$$

Results and Conclusions:

The ΔE values obtained for the different examples are summarized in Table 1 below.

TABLE 1

| Example | Sequence of layers prior to removal | Type of surfactant comprised in the third composition | $\Delta E_{Stage2/Stage1}$[1] | $\Delta E_{Stage3/Stage2}$[2] | $\Delta E_{Stage3/Stage1}$[3] |
|---|---|---|---|---|---|
| Example 1A | PDADMAC/PSS/PEI-Red/PSS | 50 mM CTAB | 43.59 | 32.29 | 11.52 |
| Comparative Example 1A | PDADMAC/PSS/PEI-Red/PSS | 50 mM SLS | 45.71 | 5.88 | 39.95 |
| Comparative Example 2A | PDADMAC/PSS/PEI-Red/PSS | 50 mM Polysorbate 20 | 44.47 | 3.79 | 40.98 |
| Comparative Example 3A | PDADMAC/PSS/PEI-Red/PSS | None | 44.00 | 0.58 | 44.33 |

[1] corresponds to the overall change of colour measured between stage 2 and stage 1
[2] corresponds to the overall change of colour measured between stage 3 and stage 2
[3] corresponds to the overall change of colour measured between stage 3 and stage 1

When comparing the ΔE values obtained for the different examples, it can be noticed that $\Delta E_{Stage3/Stage\ 1}$ is much lower for Example 1A than for the other examples. This shows that the amount of colour which is removed is much higher when the third composition comprises one or more cationic surfactants) and therefore demonstrates that it is easier to remove the polymeric layer which is obtained by successively applying the first and the second compositions as well as any coloured layer obtained on top of this polymeric layer by applying a third composition comprising one or more cationic polymer(s).

Second Set of Experimental Data—Examples of Methods According to the Present Invention wherein Different Concentrations of Cationic Surfactants have been Used in the Third Composition Example 2A A hair swatch has been treated as in example 1A except that the third composition has been replaced with the following third composition:

| Third Composition | |
|---|---|
| Ingredients | g/l |
| CTAB | 3.64 (0.01 mol/l) | pH was not adjusted

Example 2B

A hair swatch has been treated as in example 1A except that the third composition has been replaced with the following third composition:

| Third Composition | |
|---|---|
| Ingredients | g/l |
| CTAB | 9.11 (0.025 mol/l) | pH was not adjusted

L*, a*, b* Measurements

The colorimetric parameters in the CIE L* a* b* system have been measured for each of the hair swatches obtained in Examples 2A and 2B as described in the first set of experimental data.

Results and Conclusions:

The ΔE values obtained for Examples 2A and 2B are summarized in Table 2 below and are compared with the ΔE values obtained for Example 1A:

TABLE 2

| Example | Sequence of layers prior to removal | Type of surfactant comprised in the third composition | $\Delta E_{Stage2/Stage1}$[1] | $\Delta E_{Stage3/Stage2}$[2] | $\Delta E_{Stage3/Stage1}$[3] |
|---|---|---|---|---|---|
| Example 2A | PDADMAC/PSS/PEI-Red/PSS | 10 mM CTAB | 43.09 | 17.00 | 26.39 |
| Example 2B | PDADMAC/PSS/PEI-Red/PSS | 25 mM CTAB | 44.50 | 25.65 | 19.01 |
| Example 1A | PDADMAC/PSS/PEI Red/PSS | 50 mM CTAB | 43.59 | 32.29 | 11.52 |

[1] corresponds to the overall change of colour measured between stage 2 and stage 1
[2] corresponds to the overall change of colour measured between stage 3 and stage 2
[3] corresponds to the overall change of colour measured between stage 3 and stage 1

When comparing the ΔE values obtained for the different examples, it can be noticed that $\Delta E_{Stage3/Stage1}$ is lower for Example 2B than for Example 2A and $\Delta E_{Stage3/Stage1}$ is lower for Example 1A than for Example 2B. This shows that the amount of colour which is removed is higher when the third composition comprises a higher concentration of cationic surfactant and therefore demonstrates that it is easier to remove the polymeric layer which is obtained by successively applying the first and the second compositions as well as any coloured layer obtained on top of this polymeric layer by applying a third composition comprising a higher concentration of cationic polymer.

Third Set of Experimental Data—Examples of Methods According to the Present Invention wherein Different Types of Cationic Surfactants have been Used in the Third Composition

Example 3A

A hair swatch has been treated as in example 1A except that the third composition has been replaced with the following third composition:

| Third Composition | |
|---|---|
| Ingredients | g/l |
| CTAB | 3.64 (0.01 mol/l) | pH was not adjusted

Example 3B

A hair swatch has been treated as in example 1A except that the third composition has been replaced with the following third composition:

| Third Composition | |
|---|---|
| Ingredients | g/l |
| TTAB | 3.36 (0.01 mol/l) | pH was not adjusted

Example 3C

A hair swatch has been treated as in example 1A except that the third composition has been replaced with the following third composition:

| Third Composition | |
|---|---|
| Ingredients | g/l |
| DoTAB | 3.08 (0.01 mol/l) | pH was not adjusted

L*, a*, b* Measurements

The colorimetric parameters in the CIE L* a* b* system have been measured for each of the hair swatches obtained in Examples 3A, 3B and 3C as described in the first set of experimental data.

Results and Conclusions:

The ΔE values obtained for Examples 3A, 3B and 3C are summarized in Table 3 below:

TABLE 3

| Example | Sequence of layers prior to removal | Type of surfactant comprised in the third composition | $\Delta E_{Stage2/Stage1}$[1] | $\Delta E_{Stage3/Stage2}$[2] | $\Delta E_{Stage3/Stage1}$[3] |
|---|---|---|---|---|---|
| Example 3A | PDADMAC/PSS/PEI-Red/PSS | 10 mM CTAB | 43.09 | 17.00 | 26.39 |
| Example 3B | PDADMAC/PSS/PEI-Red/PSS | 10 mM TTAB | 43.60 | 14.64 | 29.34 |
| Example 3C | PDADMAC/PSS/PEI-Red/PSS | 10 mM DoTAB | 45.54 | 8.20 | 37.53 |

[1] corresponds to the overall change of colour measured between stage 2 and stage 1
[2] corresponds to the overall change of colour measured between stage 3 and stage 2
[3] corresponds to the overall change of colour measured between stage 3 and stage 1

When comparing the ΔE values obtained for the different examples, it can be noticed that $\Delta E_{Stage3/Stage1}$ is lower for Example 3B than for Example 3C and $\Delta E_{Stage3/Stage1}$ is lower for Example 3A than for Example 3B. This shows that the amount of colour which is removed is higher when the cationic surfactant comprised in the third composition comprises a group which has a higher number of carbon atoms and therefore demonstrates that it is easier to remove the polymeric layer which is obtained by successively applying the first and the second compositions as well as any coloured layer obtained on top of this polymeric layer by applying a third composition comprising a cationic polymer which comprises a group having a higher number of carbon atoms.

Fourth Set of Experimental Data—Examples of Methods According to the Present Invention wherein Different Types of Anionic Polymers have been Used in the Second and Fifth Compositions

Example 4A

A hair swatch has been treated as in example 1A except that the second and fifth compositions have been replaced with the following composition:

| Second or Fifth Composition | |
|---|---|
| Ingredients | g/l |
| DxS | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

Example 4B

A hair swatch has been treated as in example 1A except that the second and fifth compositions have been replaced with the following composition:

| Second or Fifth Composition | |
|---|---|
| Ingredients | g/l |
| PAA | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

Example 4C

A hair swatch has been treated as in example 1A except that the second and fifth compositions have been replaced with the following composition:

| Second or Fifth Composition | |
|---|---|
| Ingredients | g/l |
| PMAA | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

Example 4D

A hair swatch has been treated as in example 1A except that the second and fifth compositions have been replaced with the following composition:

| Second or Fifth Composition | |
|---|---|
| Ingredients | g/l |
| Sodium alginate | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

Example 4E

A hair swatch has been treated as in example 1A except that xe second and fifth compositions have been replaced with the following composition:

| Second or Fifth Composition | |
|---|---|
| Ingredients | g/l |
| PSS-PS | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl $L^*$, $a^*$, $b^*$ Measurements The colorimetric parameters in the CIE $L^*$ $a^*$ $b^*$ system have been measured for each of the hair swatches obtained in Examples 4A, 4B, 4C, 4D and 4E as described in the first set of experimental data, Results and Conclusions:

The $\Delta E$ values obtained for Examples 4A, 4B, 4C, 4D and 4E are summarized in Table 4 below and are compared with the $\Delta E$ values obtained for Example 1A:

TABLE 4

| Example | Sequence of layers prior to removal | Type of surfactant comprised in the third composition | $\Delta E_{Stage2/Stage1}$[1] | $\Delta E_{Stage3/Stage2}$[2] | $\Delta E_{Stage3/Stage1}$[3] |
|---|---|---|---|---|---|
| Example 1A | PDADMAC/PSS/PEI-Red/PSS | 50 mM CTAB | 43.59 | 32.29 | 11.52 |
| Example 4A | PDADMAC/DxS/PEI-Red/DxS | 50 mM CTAB | 46.41 | 17.19 | 29.68 |
| Example 4B | PDADMAC/PAA/PEI-Red/PAA | 50 mM CTAB | 48.03 | 13.69 | 34.77 |
| Example 4C | PDADMAC/PMAA/PEI-Red/PMAA | 50 mM CTAB | 45.29 | 12.28 | 33.49 |
| Example 4D | PDADMAC/Alginate/PEI-Red/Alginate | 50 mM CTAB | 47.33 | 11.05 | 36.82 |
| Example 4E | PDADMAC/PSS-PS/PEI-Red/PSS-PS | 50 mM CTAB | 40.77 | 29.74 | 11.11 |

[1] corresponds to the overall change of colour measured between stage 2 and stage 1
[2] corresponds to the overall change of colour measured between stage 3 and stage 2
[3] corresponds to the overall change of colour measured between stage 3 and stage 1

When comparing the ΔE values obtained for the different examples, it can be noticed that $\Delta E_{Stage3/Stage1}$ is lower for Examples 1A and 4E than for the other examples. This shows that the amount of colour which is removed is higher when the first anionic polymer is more hydrophobic, i.e. when it comprises one or more functional group(s) per polymer chain selected from the group consisting of phenyl group, alkyl groups comprising at least 8 carbon atoms and mixtures thereof and therefore demonstrates that it is easier to remove the polymeric layer which is obtained by successively applying the first and the second compositions as well as any coloured layer obtained on top of this polymeric layer when the first anionic polymer is more hydrophobic.

Fifth Set of Experimental data—Examples of Methods According to the Present Invention wherein Different Types of Cationic Polymers have been Used in the First and Fourth Compositions

Example 5A

A hair swatch has been treated as in example 1A except that the first composition has been replaced with the following composition:

| First Composition | |
|---|---|
| Ingredients | g/l |
| PAH | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

L*, a*, b* Measurements

The colorimetric parameters in the CIE L* a* b* system have been measured for each of the hair swatches obtained in Examples 5A and 5B as described in the first set of experimental data, Results and Conclusions:

The ΔE values obtained for Examples 5A and 5B are summarized in Table 5 below and are compared with the ΔE values obtained for Example 1A:

TABLE 5

| Example | Sequence of layers prior to removal | Type of amino functional group comprised by the cationic polymer comprised in the first composition | $\Delta E_{Stage2/Stage1}$[1] | $\Delta E_{Stage3/Stage2}$[2] | $\Delta E_{Stage3/Stage1}$[3] |
|---|---|---|---|---|---|
| Example 1A | PDADMAC/PSS/PEI-Red/PSS | Quaternary | 43.59 | 32.29 | 11.52 |
| Example 5A | PEI/PSS/PEI-Red/PSS | Primary/Secondary/Tertiary | 44.84 | 31.84 | 13.19 |
| Example 5B | PAH/PSS/PEI-Red/PSS | Primary | 39.09 | 23.57 | 15.60 |

[1] corresponds to the overall change of colour measured between stage 2 and stage 1
[2] corresponds to the overall change of colour measured between stage 3 and stage 2
[3] corresponds to the overall change of colour measured between stage 3 and stage 1

| First Composition | |
|---|---|
| Ingredients | g/l |
| PEI | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

Example 5B

A hair swatch has been treated as in example 1A except that the first composition has been replaced with the following composition:

When comparing the ΔE values obtained for the different examples, it can be noticed that $\Delta E_{Stage3/Stage1}$ is lower for Example 1A than for Example 5A and $\Delta E_{Stage3/Stage1}$ is lower for Example 5A than for Example 5B. This shows that the amount of colour which is removed is higher when the first cationic polymer comprised in the first composition comprises one or more amino functional group(s) per polymer chain selected from the group consisting of secondary, tertiary, quaternary amino functional groups and mixtures thereof and even higher when the cationic surfactant comprised in the first composition comprises one or more amino functional group(s) per polymer chain selected from quaternary amino functional groups and therefore demonstrates that it is easier to remove the first polymeric layer which is obtained by successively applying the first and the second compositions as well as any coloured layer obtained on top of this polymeric layer by using a first composition comprising a first cationic polymer which comprises one or more amino functional group(s) per polymer chain selected from the group consisting of secondary, tertiary, quaternary amino functional groups and mixtures thereof, preferably from quaternary amino functional groups.

Sixth Set of Experimental Data—Examples of Methods According to the Present Invention wherein Either the First Composition Comprises a Cationic Coloured Polymer Polymer or the Second Composition Comprises an Anionic Coloured Polymer

Example 6A

| First Composition | |
|---|---|
| Ingredients | g/l |
| PDADMAC | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

| Second Composition | |
|---|---|
| Ingredients | g/l |
| PSS-Red | 5.00 (0.5 wt %) |
| NaCl | 11.69 (0.2 mol/l) |
| Triethanolamine | 7.46 (0.05 mol/l) |
| Cellosize (TM) hydroxyethyl cellulase QP-4400H, Dow Chemicals | 5.00 (0.5 wt %) | pH adjusted to 8 by adding 1.0 mol/l NaOH or 1.0 mol/l HCl

| Fourth Composition | |
|---|---|
| Ingredients | g/l |
| PEI-Blue | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

| Fifth Composition | |
|---|---|
| Ingredients | g/l |
| PSS | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

| Third Composition | |
|---|---|
| Ingredients | g/l |
| CTAB | 18.22 (0.05 mol/l) | pH was not adjusted

Step 1: Formation of the Polymeric Layer and the Coloured Layer on Top of the Polymeric Layer:

A hair swatch has been treated according to the following protocol:
(i) Preparing the first, second, fourth and fifth compositions shortly before application;
(ii) Applying 4 mL of the first composition to the hair swatch with a brush and wrapping the hair swatch with a commercial kitchen plastic wrap;
(iii) Agitating the first composition with the hair swatch in plastic wrap for 15 min at 55° C. in a laboratory-type drying cabinet;
(iv) Rinsing the hair swatch for 30 s with ruing lukewarm tap water at a temperature of 30° C. to 35° C.;
(v) Applying 4 mL of the second composition to the hair swatch with a brush and wrapping the hair swatch with a commercial kitchen plastic wrap;
(vi) Agitating the second composition with the hair swatch in plastic wrap for 15 min at 55° C. in a laboratory-type drying cabinet;
(vii) Rinsing the hair swatch for 30 s with running lukewarm tap water at a temperature of 30° C. to 35° C.;
(viii) Applying 4 mL of the fourth composition to the hair swatch with a brush and Trapping the hair swatch with a commercial kitchen plastic wrap;
(ix) Agitating the fourth composition with the hair swatch in plastic wrap for 15 min at 55° C. in a laboratory-type drying cabinet;
(x) Rinsing the hair swatch for 30 s with running lukewarm tap water at a temperature of 30° C. to 35° C.;
(xi) Applying 4 mL of the fourth composition to the hair swatch with a brush and wrapping the hair swatch with a commercial kitchen plastic wrap;
(xii) Agitating the fourth composition with the hair swatch in plastic wrap for 15 min at 55° C. in a laboratory-type drying cabinet;
(xiii) Rinsing the hair swatch for 30 s with running lukewarm tap water at a temperature of 30° C. to 35° C.;
(xiv) Drying the hair swatch first with tissue paper and then with a hair dryer.

Step 2: Removal of the Polymeric Layer

The hair swatch obtained at the end of step 1) has been then treated according to the following protocol:
(i) Applying 5 ml of the third composition to the coloured hair swatch with a brush for 30 s in a plastic bowl and letting the hair swatch soaked for 30 s;
(ii) Rinsing the hair swatch for 30 s with running lukewarm tap water at a temperature of 30° C. to 35° C.;
(iii) Drying the hair swatch first with tissue paper and then with a hair dryer.

Example 6B

A hair swatch has been treated as in example 6A except that the first and the second compositions have been replaced with the following composition:

| First Composition | |
|---|---|
| Ingredients | g/l |
| PDADMAC-Red | 5.00 (0.5 wt %) |
| NaCl | 11.69 (0.2 mol/l) |

-continued

| First Composition | |
|---|---|
| Ingredients | g/l |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

| Second Composition | |
|---|---|
| Ingredients | g/l |
| PSS | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.5 wt %) | pH adjusted to 8 by adding 1.0 mol/l NaOH or 1.0 mol/l HCl

L*, a*, b* Measurements

The colorimetric parameters in the CIE a* b* system have been measured for each of the hair swatches obtained in Examples 6A and 6B as described in the first set of experimental data.

Results and Conclusions:

The ΔE values obtained for Examples 6A and 6B are summarized in Table 6 below:

TABLE 6

| Example | Sequence of layers prior to removal | Type of surfactant comprised in the third composition | $\Delta E_{Stage2/Stage1}^{1}$ | $\Delta E_{Stage3/Stage2}^{2}$ | $\Delta E_{Stage3/Stage1}^{3}$ |
|---|---|---|---|---|---|
| Example 6A | PDADMAC/PSS-Red/PEI-Blue/PSS | 50 mM CTAB | 13.31 | 23.82 | 4.79 |
| Example 6B | PDADMAC-Red/PSS/PEI-Blue/PSS | 50 mM CTAB | 11.89 | 23.68 | 6.41 |

When comparing the ΔE values obtained for the different examples, it can be noticed that $\Delta E_{Stage3/Stage\ 1}$ is lower for Example 6A than for Example 6B. This shows that the amount of colour that is removed is higher when the coloured polymer is comprised in the second composition and therefore demonstrates that the interaction between the cationic surfactant comprised in the third composition and the first anionic polymer comprised in the second composition which is applied to the hair is stronger than the interaction between the first cationic polymer comprised in the first composition which is applied to the hair and the first anionic polymer comprised in the second composition which is applied to the hair. This stronger interaction between the cationic surfactant comprised in the third composition and the first anionic polymer comprised in the second composition which is applied to the hair makes easier the removal of a portion of the first polymeric layer and of any coloured layers which could be obtained thereafter on top of the first polymeric layer.

In view of the above, a method, kit, use, and composition for decolouring hair which is coloured with a polymeric single layer, a polymeric double-layer having two polymeric sublayers, or a polymeric multi-layer having a plurality of polymeric sublayers is disclosed. At least one of the polymeric layers, or sublayers, is coloured. For example, the first cationic polymeric layer, or sublayer, formed by the first cationic polymer can be coloured using a cationic coloured polymer. The first anionic polymer used to form the first anionic polymeric layer, or sublayer, can be coloured or can be uncoloured.

In the broadest sense, at least one of the one, two, three, four or multiple polymeric layers or sublayers is coloured. For example, the first cationic polymeric sublayer is coloured, and the optional first anionic polymeric sublayer is uncoloured. A further example includes a first cationic uncoloured sublayer, a first anionic uncoloured sublayer, a second cationic coloured sublayer, and a second uncoloured, or coloured, anionic sublayer, in this order.

The coloured polymeric layer, such as a cationic coloured polymeric layer, or coloured polymeric sublayers can be removed by applying the third composition having one or more cationic surfactant(s). The hair that was coloured with the coloured polymeric layer or coloured polymeric sublayer or sublayers is decoloured and appears in its natural colour.

The third composition containing a cationic surfactant can therefore be used to remove the coloured polymeric layer, the coloured polymeric sublayer of a polymeric double layer, or a coloured polymeric sublayer of a polymeric multi-layer.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. A method for temporarily coloring hair strands comprising steps A, B, C and D in an ordered, time separated sequence:
    A) applying to the hair strands a first composition to form a first coating of a first composition on the hair strands wherein the first composition comprises one or more first uncolored cationic amine polymer(s) having a charge density of at least 0.3 per monomer unit;
    B) applying to the first coating immediately after step A, a second composition to overcoat the first coating and form a dual layer coating wherein the second composition comprises one or more first uncolored anionic polymer(s) having a charge density of at least 0.8 per monomer unit at full deprotonation;
    C) applying to the dual layer coating immediately after step B, a fourth composition to form a colored coating on the hair strands, wherein the fourth composition comprises a one or more colored cationic polymer(s) having at least one kind of pendant covalently bonded chromophore or fluorophore wherein the one or more colored cationic polymers are the protonated forms of the corresponding polymers having at least one kind of pendant covalently bonded chromophore or fluorophore and having in chain and/or pendant primary and secondary amine groups which form cationic ammonium groups by protonation and wherein the one or more colored cationic polymer(s) have a charge density of at least 0.3 when fully protonated and negligible charge density when fully deprotonated;
D) applying to the colored coating at a pH in a range of from 10.4 to 14 and at a time subsequent to the time of forming the colored coating of step C, a third composition to form a removable colored coating, wherein the third composition comprises one or more cationic surfactants comprising one or more linear or branched C8-C22 aliphatic quaternary ammonium salt(s).

2. The method according to claim 1, wherein the one or more cationic surfactant(s) are selected from quaternary ammonium salts having the following formula:

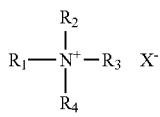

wherein:
$R_1$ is selected from the group consisting of linear or branched aliphatic groups, wherein the linear or branched aliphatic groups comprise from 6 to 22 carbon atoms; and
$R_2$ is methyl; and
$R_3$ and $R_4$ are both methyl; and
$X^-$ is an anion selected from chloride, bromide, iodide, alkyl sulfates, phosphates, alkyl sulfonates, alkylaryl sulfonates and anions derived from organic acids or amino acids.

3. The method according to claim 2, wherein the one or more cationic surfactant(s) are selected from the group consisting of cetrimonium halide, stearimonium halide, behentrimonium halide, behentrimonium halide, dodecyltrimethylammonium halide, tetradecyltrimethylammonium halide, and mixtures thereof, wherein the halide is selected from bromide and chloride.

4. The method according to claim 1, wherein the one or more first uncolored anionic polymer(s) comprise one or more functional group(s) per polymer chain selected from the group consisting of phenyl group, alkyl groups comprising at least 8 carbon atoms and mixtures thereof.

5. The method according to claim 1, wherein the one or more first uncolored anionic polymer(s) are selected from the group consisting of polystyrene sulfonate salts, λ-carrageenan salts, dextran sulfate salts, polyacrylic acid salts, poly(methacrylic acid) salts, alginic acid salts, carboxymethylcellulose salts, polystyrene sulfonate/polystyrene copolymer salts, copolymers thereof and mixtures thereof.

6. The method according to claim 1, wherein the one or more first uncolored cationic amine polymer(s) comprise one or more amino functional group(s) per polymer chain, wherein the amino functional group(s) are selected from the group consisting of primary, secondary, tertiary, quaternary amino functional groups and mixtures thereof.

7. The method according to claim 1, wherein the one or more first uncolored cationic amine polymer(s) are selected from the group consisting of polyethyleneimine, polyallylamine hydrochloride, polydiallyldimethylammonium chloride, polyvinylamine, copolymers thereof and mixtures thereof.

8. The method according to claim 1, wherein at least one of steps A, B, and C further comprises the subsequent sub-step of:
washing and/or rinsing the hair.

9. The method according to claim 1, wherein:
the first composition comprises a total concentration of one or more first uncolored cationic amine polymers ranging from 0.1 g/L to 100 g/L and/or
the second composition comprises a total concentration of one or more first uncolored anionic polymers ranging from 0.1 g/L to 100 g/L and/or
the third composition comprises a total amount of one or more cationic surfactants ranging from 0.01% to 10% by total weight of the third composition and/or
the fourth composition comprises a total amount of one or more colored cationic polymers ranging from 0.1 g/L to 100g/L.

10. The method according to claim 1 further comprising:
after the application of the fourth composition of step C and before the application of the third composition of step D carrying out the following sequence of steps:
a) applying a fifth composition comprising one or more second anionic polymer(s) to the dual layer coating overlaid with the fourth composition to form a tetra layer coating on the surfaces of the hair strands; and optionally
b) applying to the tetra layer coating on the surfaces of the hair strands a sixth composition comprising one or more second cationic amine polymer(s) having primary and secondary amine groups; and optionally
repeating steps a and b at least once, wherein the one or more second cationic amine polymer(s) are cationic coloured polymers and the one or more second anionic polymer(s) are anionic coloured polymers.

11. The method according to claim 10, wherein the one or more second anionic polymer(s) comprise one or more monomer unit(s) comprising one or more functional group(s) selected from the group consisting of sulfate, sulfonate, carboxylate, phosphate, phosphonate groups and mixtures thereof.

12. The method according to claim 10, wherein the one or more second anionic polymer(s) are selected from the group consisting of polystyrene sulfonate salts, λ-carrageenan salts, dextran sulfate salts, polyacrylic acid salts, poly(methacrylic acid) salts, alginic acid salts, carboxymethylcellulose salts, polystyrene sulfonate/polystyrene copolymer salts, copolymers thereof and mixtures thereof.

13. The method according to claim 1, wherein the unprotonated forms of the one or more colored cationic polymer(s) of the fourth composition are selected from the group consisting of polyethyleneimine, polyallylamine hydrochloride, polyvinylamine, copolymers thereof and mixtures thereof.

14. The method according to claim 1, wherein the first uncolored cationic amine polymer is protonated as its cationic form.

15. The method according to claim 1, wherein one or more of the first coating, dual layer coating and colored coating are at least partially dried following application and/or formation.

16. The method according to claim 1, further comprising washing and/or rinsing the removable colored coating with water to remove the removable colored coating from the hair strands.

17. A kit for treating hair comprising:
a first component comprising the first composition as defined in claim 1
a second component comprising the second composition as defined in claim 1 a third component comprising the third composition as defined in claim 1
a fourth component comprising the fourth composition as defined in claim 1.

* * * * *